United States Patent [19]
Van Heertum et al.

[11] Patent Number: 5,163,995
[45] Date of Patent: Nov. 17, 1992

[54] HERBICIDAL ALKOXY-1,2,4-TRIAZOLO[1,5-C]PYRIMIDINE-2-SULFONAMIDES

[75] Inventors: John C. Van Heertum, Concord, Calif.; Ben C. Gerwick, III, Carmel; William A. Kleschick, Indianapolis, both of Ind.; Timothy C. Johnson, Concord, Calif.

[73] Assignee: DowElanco, Indianapolis, Ind.

[21] Appl. No.: 744,149

[22] Filed: Aug. 13, 1991

Related U.S. Application Data

[60] Continuation-in-part of Ser. No. 529,047, May 25, 1990, abandoned, which is a division of Ser. No. 347,601, May 3, 1989, Pat. No. 5,010,195, which is a continuation-in-part of Ser. No. 198,278, May 25, 1988, abandoned.

[51] Int. Cl.$^5$ .................. A01N 43/90; C07D 471/02
[52] U.S. Cl. ........................ 71/92; 544/263; 544/315; 544/318; 544/319
[58] Field of Search .................. 71/92; 544/263

[56] References Cited

U.S. PATENT DOCUMENTS

| | | | |
|---|---|---|---|
| 4,349,378 | 9/1982 | Cliff et al. | 71/92 |
| 4,528,288 | 7/1985 | Wade | 544/263 |
| 4,755,212 | 7/1988 | Kleschick et al. | 544/263 |
| 4,904,301 | 2/1990 | Pearson et al. | 544/263 |
| 4,910,306 | 3/1920 | McKendry | 544/263 |
| 4,921,527 | 5/1990 | Tseng | 544/263 |
| 4,959,473 | 9/1990 | Pearson et al. | 544/263 |
| 4,981,507 | 1/1991 | Jelich et al. | 544/263 |
| 5,041,157 | 8/1991 | Seiler et al. | 71/92 |
| 5,071,468 | 12/1991 | Astles | 71/92 |

FOREIGN PATENT DOCUMENTS 244948 11/1987 European Pat. Off.
951652 3/1964 United Kingdom .................. 544/263

OTHER PUBLICATIONS

Brown et al., *Aust. J. Chem.*, 32, 2713–2726 (1979).
Miller et al., *J. Chem. Soc.*, 1963, 5642–5659.

*Primary Examiner*—Donald G. Daus
*Attorney, Agent, or Firm*—D. Wendell Osborne

[57] ABSTRACT

5-Alkoxy-1,2,4-triazolo[1,5-c]pyrimidine-2-sulfonamides are prepared from 5-alkoxy-1,2,4-triazolo[1,5-c]pyrimidine-2-sulfonyl halides by condensation with ortho-substituted N-trialkylsilylanilines and by other methods. N-(2,6-dichloro-3-methylphenyl)-8-fluoro-5-methoxy-1,2,4-triazolo[1,5-c]pyrimidine-2-sulfonamide is typical. The compounds are general and selective pre- and postemergence herbicides.

73 Claims, No Drawings

HERBICIDAL ALKOXY-1,2,4-TRIAZOLO[1,5-C]PYRIMIDINE-2-SULFONAMIDES

CROSS-REFERENCE TO RELATED APPLICATION

This application is a continuation-in-part of Ser. No. 07/529,047, filed May 25, 1990, which is a divisional of Ser. No. 07/347,601, filed May, 3, 1989, now U.S. Pat. No. 5,010,195, which is a continuation-in-part of Ser. No. 198,278, filed May 25, 1988, now abandoned.

BACKGROUND OF THE INVENTION

The present invention relates to novel alkoxy substituted 1,2,4-triazolo[1,5-c]pyrimidine-2-sulfonamide compounds, to herbicidal compositions containing the compounds, and to the utility of the compounds for the control of unwanted vegetation.

The control of unwanted vegetation by means of chemical agents, i.e., herbicides, is an important aspect of modern agriculture and land management. While many chemicals that are useful in unwanted vegetation control are known, new compounds that are more effective generally or for specific plant species, are less damaging to desirable vegetation, are safer to man or the environment, are less expensive to use, or have other advantageous attributes are desirable.

It is known that certain 1,2,4-triazolo[1,5-a]pyrimidine-2-sulfonamides possess herbicidal activity (U.S. Pat. No. 4,886,883). The compounds are effective against unwanted vegetation when applied to the vegetation or its locus either preemergence or postemergence. Various methods for the preparation of these herbicides and for the preparation of the requisite intermediates are also reported. 1,2,4-Triazolo-[1,5-a]-1,3,5-triazine-2-sulfonamides possessing herbicidal properties are also known (U.S. Pat. No. 4,605,433) as are imidazolo[1,2-a]pyrimidine-2-sulfonamides (U.S. Pat. No. 4,731,446) and pyrazolo[1,5-a]pyrimidine-2-sulfonamides (U.S. Pat. No. 4,992,091).

SUMMARY OF THE INVENTION

It has now been found that alkoxy substituted 1,2,4-triazolo[1,5-c]pyrimidine-2-sulfonamides of the formula

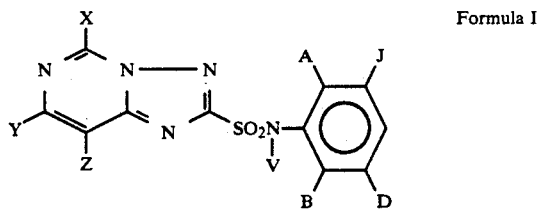

Formula I wherein
X represents OR, H, $CH_3$, $SCH_3$, or $CF_3$;
Y represents OR, H, $CH_3$, Cl, Br, F, or $CF_3$; and
Z represents OR, H, $CH_3$, $CF_3$, Cl, Br, or F;
with the proviso that at least one of X, Y, and Z represents OR; and
A represents F, Cl, Br, C(O)E, $C_1$-$C_4$ haloalkyl, $NO_2$, CN, $SOR^3$, or $SO_2R^3$;
B represents H, R, F, Cl, Br, CN, $OR^3$, $SR^3$, $NR^1R^2$, phenyl, phenoxy, or phenylthio, each phenyl, phenoxy, or phenylthio optionally possessing 1 to 3 substituents selected from the group consisting of F, Cl, Br, CN, $CF_3$, $NO_2$, and $CH_3$;
D and J each represent H or $CH_3$, with the proviso that at least one of D and J represents H:
V represents H or $C(O)R^3$;
R represents $C_1$-$C_3$ alkyl;
$R^1$ and $R^2$ each, independently represent H or $C_1$-$C_4$ alkyl:
$R^3$ represents $C_1$-$C_4$ alkyl or $C_1$-$C_4$ haloalkyl:
E represents $OR^1$ or $NR^1R^2$; and,
when V represents H, the agriculturally acceptable salts thereof are useful in the control of unwanted vegetation and can be employed for control of unwanted vegetation in the presence of grassy crops and soybeans. The compounds of Formula I, usually in the form of herbicidal compositions containing them in addition to an agriculturally acceptable adjuvant or carrier, exhibit herbicidal properties when applied either directly to the unwanted vegetation or to the locus thereof and when applied either preemergence or postemergence.

DETAILED DESCRIPTION OF THE INVENTION

The compounds of the present invention include the alkoxy substituted 1,2,4-triazolo[1,5-c]pyrimidine-2-sulfonamides of Formula I wherein A, B, D, J, V, X, Y, and Z are as defined hereinabove. Each of these compounds contains at least one alkoxy substituent on the pyrimidine ring and has an electron withdrawing substituent in one or both of the 2- and 6-positions of the aniline ring. The invention also includes the related compounds of Formula I wherein X represents Cl, Br, or F that can be used as intermediates for the preparation of such compounds wherein X represents OR or $SCH_3$.

While each of the 1,2,4-triazolo[1,5-c]pyrimidine-2-sulfonamide compounds described by Formula I is within the scope of the invention, the degree of herbicidal activity and the spectrum of weed control obtained varies depending upon the substituents present and, consequently, certain of the compounds are preferred. Compounds of Formula I wherein at least one of X, Y, and Z represents methoxy or ethoxy (R of OR represents methyl or ethyl) are usually preferred. Compounds of Formula I in which one or both of X and Y represents methoxy or ethoxy are often more preferred and compounds wherein X represents methoxy or ethoxy are especially preferred. Compounds wherein both X and Y represent methoxy or ethoxy are also sometimes preferred. Additionally, compounds wherein Y and/or Z represents hydrogen, chloro, bromo, or fluoro are sometimes preferred. Compounds of Formula I having at least one electron withdrawing substituent, chosen from the substituents specified for A and B above, in an ortho position of the aniline ring are within the scope of the invention. Those in which A represents fluoro, chloro, bromo, nitro, $CO_2R^1$, $CONR^1R^2$, or trifluoromethyl are usually preferred. Additionally, those compounds of Formula I wherein B represents hydrogen, fluoro, chloro, bromo, methyl, methoxy, or methylthio are generally preferred as are compounds wherein J represents hydrogen. Compounds wherein V represents hydrogen and the agriculturally acceptable salts derived therefrom are normally preferred as well.

The term alkyl as used herein includes straight chain and branched chain moieties. Thus, typical alkyl groups are methyl, ethyl, 1-methylethyl, 1,1-dimethylethyl, propyl, 2-methylpropyl, 1-methylpropyl, and butyl.

The term haloalkyl includes alkyl moieties having one or a multiplicity of halogen substituents, selected independently from fluorine, chlorine, and bromine. Fluorine is a preferred halogen and trifluoromethyl is a preferred $C_1$-$C_4$ haloalkyl moiety. A listing of some typical compounds of the invention is given in Table 1.

TABLE 1

1,2,4-TRIAZOLO[1,5-c]PYRIMIDINE-2-SULFONAMIDES

| Cpd. No. | X | Y | Z | V | A | B | D | J | Melting Point, °C. | Elem. Anal. |
|---|---|---|---|---|---|---|---|---|---|---|
| 1 | $OCH_3$ | $OCH_3$ | H | H | Cl | Cl | H | H | 211-212 | CHN |
| 2 | $OCH_3$ | $OCH_3$ | H | H | Cl | Cl | $CH_3$ | H | 212-213 | CHN |
| 3 | $OCH_3$ | $OCH_3$ | Br | H | Cl | Cl | H | H | 225-226(d) | CHN |
| 4 | $OCH_3$ | $OCH_3$ | Br | H | Cl | Cl | $CH_3$ | H | 228-229(d) | CHN |
| 5 | $OCH_3$ | $OCH_3$ | H | H | F | F | H | H | 198-199(d) | CHN |
| 6 | $OC_2H_5$ | Cl | H | H | $SO_2CH_3$ | F | H | H | 300(d) | CHN |
| 7 | $OCH_3$ | H | $CH_3$ | H | $CO_2CH_3$ | F | H | H | 175-178(d) | CHN |
| 8 | $OCH_3$ | H | Cl | H | F | $SCH_3$ | H | H | 192-195(d) | CHN |
| 9 | $OCH_3$ | F | H | H | $CF_3$ | H | H | H | 147-152(d) | CHN |
| 10 | $OC_2H_5$ | Cl | Cl | H | $CO_2CH_3$ | F | H | H | 193-194(d) | CHN |
| 11 | $OC_2H_5$ | Cl | Cl | H | Cl | Cl | H | H | 238-239(d) | CHN |
| 12 | $OCH_3$ | Cl | Cl | H | F | F | $CH_3$ | H | 179-181(d) | CHN |
| 13 | $OCH_3$ | H | H | H | $NO_2$ | $CH_3$ | $CH_3$ | H | 214-216(d) | CHN |
| 14 | $OCH_3$ | H | H | H | Cl | $OCH_3$ | H | H | 190-192(d) | CHN |
| 15 | $OCH_3$ | $CH_3$ | H | H | Cl | Cl | H | H | 208-209 | CHN |
| 16 | $OCH_3$ | $CH_3$ | H | H | Cl | Cl | $CH_3$ | H | 221-222 | CHN |
| 17 | $OCH_3$ | $CH_3$ | H | H | F | F | H | H | 187-188 | CHN |
| 18 | $OC_3H_7(i)$ | F | H | H | $CO_2CH_3$ | Cl | H | H | 197-198(d) | CHN |
| 19 | $OC_3H_7(n)$ | F | H | H | $CF_3$ | $OCH_3$ | H | H | 159-163 | CHN |
| 20 | $OCH_3$ | Br | H | H | Cl | Cl | H | H | 212-213(d) | CHN |
| 21 | $OC_2H_5$ | H | Cl | H | Cl | Cl | H | H | 240-242(d) | CHN |
| 22 | $OC_2H_5$ | H | Cl | H | F | F | $CH_3$ | H | 225-226(d) | CHN |
| 23 | $OCH_3$ | H | Br | H | F | F | H | H | 207-210(d) | CHN |
| 24 | $OCH_3$ | H | Br | H | $CO_2CH_3$ | F | H | H | 195-197(d) | CHN |
| 25 | $OC_2H_5$ | F | H | H | $NO_2$ | $CH_3$ | H | H | 219-220(d) | CHN |
| 26 | $OC_2H_5$ | $CH_3$ | H | H | F | F | $CH_3$ | H | 203-205 | CHN |
| 27 | $OC_2H_5$ | $CH_3$ | H | H | $NO_2$ | $CH_3$ | H | H | 225-227 | CHN |
| 28 | $OC_2H_5$ | $CH_3$ | H | H | $CO_2CH_3$ | Cl | H | H | 234-238 | CHN |
| 29 | $CH_3$ | $OCH_3$ | Cl | H | Cl | Cl | H | H | 234-236(d) | CHN |
| 30 | $CH_3$ | $OCH_3$ | Cl | H | Cl | Cl | $CH_3$ | H | 231-232 | CHN |
| 31 | $CH_3$ | $OCH_3$ | Cl | H | F | F | H | H | 219-220 | CHN |
| 32 | $CH_3$ | $OCH_3$ | Cl | H | $NO_2$ | $CH_3$ | H | H | 216-218 | CHN |
| 33 | $OCH_3$ | $OCH_3$ | Cl | H | Cl | Cl | H | H | 234-235(d) | CHN |
| 34 | $OCH_3$ | $OCH_3$ | Cl | H | Cl | Cl | $CH_3$ | H | 214-215(d) | CHN |
| 35 | $OCH_3$ | $OCH_3$ | Cl | H | F | F | H | H | 245-246(d) | CHN |
| 36 | $OC_2H_5$ | F | H | H | $CO_2CH_3$ | $CH_3$ | H | H | 190-191(d) | CHN |
| 37 | $OC_2H_5$ | F | H | H | $NO_2$ | $CH_3$ | $CH_3$ | H | 219-220(d) | CHN |
| 38 | $OC_2H_5$ | F | H | H | $CO_2CH_3$ | Cl | H | H | 222-223(d) | CHN |
| 39 | $OC_2H_5$ | F | H | H | F | Cl | H | H | 212-213(d) | CHN |
| 40 | $OC_2H_5$ | F | H | H | $CF_3$ | $OCH_3$ | H | H | 212-213(d) | CHN |
| 41 | $OCH_3$ | H | H | H | F | F | H | H | 198-199(d) | CHN |
| 42 | $OCH_3$ | H | H | H | Cl | Cl | H | H | 206-207(d) | CHN |
| 43 | $OCH_3$ | H | H | H | Cl | Cl | $CH_3$ | H | 215-216(d) | CHN |
| 44 | $OCH_3$ | $CH_3$ | H | H | $CO_2CH_3$ | F | H | H | 175-177 | CHN |
| 45 | $OCH_3$ | $CH_3$ | H | H | Cl | $CH_3$ | H | H | 185-235 | CHN |
| 46 | $OC_2H_5$ | $CH_3$ | H | H | Cl | Cl | H | H | 234-235 | CHN |
| 47 | $OC_2H_5$ | $CH_3$ | H | H | $CO_2CH_3$ | F | H | H | 180-185 | CHN |
| 48 | $OC_2H_5$ | $CH_3$ | H | H | F | F | H | H | 201-205 | CHN |
| 49 | $OCH_3$ | $CH_3$ | Cl | H | Cl | Cl | $CH_3$ | H | 210-211 | CHN |
| 50 | $OCH_3$ | $CH_3$ | Cl | H | F | F | H | H | 205-206 | CHN |
| 51 | $OCH_3$ | $CH_3$ | Cl | H | Cl | Cl | H | H | 240-241 | CHN |
| 52 | $OCH_3$ | $CF_3$ | H | H | Cl | Cl | H | H | 221-222 | CHN |
| 53 | $OCH_3$ | $CF_3$ | H | H | F | F | H | H | 188-189 | CHN |
| 54 | $OCH_3$ | $CF_3$ | H | H | Cl | Cl | $CH_3$ | H | 233-234 | CHN |
| 55 | $OCH_3$ | $OCH_3$ | Cl | H | $CO_2CH_3$ | F | H | H | 208-209(d) | CHN |
| 56 | $OCH_3$ | $OCH_3$ | H | H | $CO_2CH_3$ | F | H | H | 166-167(d) | CHN |
| 57 | $CH_3$ | $OCH_3$ | H | H | F | F | H | H | 208-209 | CHN |
| 58 | $CH_3$ | $OCH_3$ | H | H | Cl | Cl | $CH_3$ | H | 150-152 | CHN |
| 59 | $CH_3$ | $OCH_3$ | H | H | Cl | Cl | H | H | 169-171 | CHN |
| 60 | $CH_3$ | $OCH_3$ | Cl | H | Br | H | H | H | 165-166 | CHN |
| 61 | $CH_3$ | $OCH_3$ | Cl | H | $CF_3$ | H | H | H | 128-130 | CHN |
| 62 | $OCH_3$ | Cl | $OCH_3$ | H | Cl | Cl | H | H | 229-230(d) | CHN |
| 63 | $OCH_3$ | Cl | $OCH_3$ | H | Cl | Cl | $CH_3$ | H | 211-212 | CHN |

TABLE 1-continued 1,2,4-TRIAZOLO[1,5-c]PYRIMIDINE-2-SULFONAMIDES

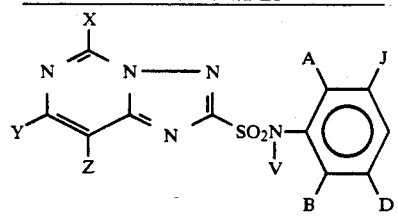

| Cpd. No. | X | Y | Z | V | A | B | D | J | Melting Point, °C. | Elem. Anal. |
|---|---|---|---|---|---|---|---|---|---|---|
| 64 | OCH3 | Cl | OCH3 | H | F | F | H | H | 193-194 | CHN |
| 65 | OC2H5 | Cl | H | H | Cl | Cl | H | H | 125-126(d) | CHN |
| 66 | OC2H5 | Cl | H | H | Cl | Cl | CH3 | H | 212-213(d) | CHN |
| 67 | OC2H5 | Cl | H | H | F | F | H | H | 219-220(d) | CHN |
| 68 | OC2H5 | Cl | H | H | CO2CH3 | F | H | H | 166-167(d) | CHN |
| 69 | OC2H5 | Cl | H | H | CF3 | H | H | H | 56-157(d) | CHN |
| 70 | OC2H5 | Cl | H | H | F | H | CH3 | H | 159-160 | CHN |
| 71 | OC2H5 | Cl | H | H | NO2 | CH3 | CH3 | H | 237-238(d) | CHN |
| 72 | OC2H5 | F | H | H | Cl | Cl | H | H | 234-235(d) | CHN |
| 73 | OC2H5 | F | H | H | CO2CH3 | F | H | H | 183-184(d) | CHN |
| 74 | OCH3 | Cl | H | H | Cl | Cl | H | H | 205-206(d) | CHN |
| 75 | OCH3 | Cl | H | H | Cl | Cl | CH3 | H | 225-226(d) | CHN |
| 76 | OCH3 | Cl | H | H | F | F | H | H | 179-180(d) | CHN |
| 77 | OCH3 | Cl | H | H | CO2CH3 | F | H | H | 185-186(d) | CHN |
| 78 | OCH3 | Cl | H | H | CF3 | H | H | H | 189-190(d) | CHN |
| 79 | OCH3 | Cl | H | H | F | H | CH3 | H | 164-165(d) | CHN |
| 80 | OCH3 | Cl | H | H | NO2 | CH3 | CH3 | H | 113-114(d) | CHN |
| 81 | OCH3 | Cl | H | H | CO2CH3 | CH3 | H | H | 148-149(d) | CHN |
| 82 | OCH3 | Cl | H | H | Br | Br | H | H | 194-195(d) | CHN |
| 83 | OCH3 | Cl | H | H | NO2 | H | H | H | 195-196(d) | CHN |
| 84 | OCH3 | Cl | H | H | CO2N(CH3)2 | F | H | H | 165-166(d) | CHN |
| 85 | OCH3 | Cl | H | H | Cl | CH3 | H | H | 175-176(d) | CHN |
| 86 | OCH3 | Cl | H | H | Br | H | H | H | 172-174(d) | CHN |
| 87 | OCH3 | Cl | H | H | CO2-i-C5H7 | F | H | H | 147-150(d) | CHN |
| 88 | OCH3 | Cl | H | H | CO2CH3 | Cl | H | H | 217-218(d) | CHN |
| 89 | OCH3 | Cl | H | H | CO2CH3 | OCH3 | H | H | 178-179(d) | CHN |
| 90 | OCH3 | Cl | H | H | CF3 | OCH3 | H | H | 177-178(d) | CHN |
| 91 | OCH3 | Cl | H | H | Cl | OCH3 | H | H | 162-164 | CHN |
| 92 | OCH3 | Cl | H | H | NO2 | CH3 | H | H | 205-206(d) | CHN |
| 93 | OCH3 | Cl | H | H | CO2C2H5 | Cl | H | H | 191-192(d) | CHN |
| 94 | OCH3 | Cl | H | H | F | F | CH3 | H | 178-179(d) | CHN |
| 95 | OCH3 | Cl | H | H | F | H | H | H | 179-180(d) | CHN |
| 96 | OCH3 | F | H | H | Cl | Cl | H | H | 201-202(d) | CHN |
| 97 | OCH3 | F | H | H | F | F | H | H | 179-180(d) | CHN |
| 98 | OCH3 | F | H | H | CO2CH3 | F | H | H | 180-182 | CHN |
| 99 | OCH3 | H | Cl | H | Cl | Cl | H | H | 229-230 | CHN |
| 100 | OCH3 | H | Cl | H | Cl | Cl | CH3 | H | 203-205 | CHN |
| 101 | OCH3 | H | Cl | H | F | F | H | H | 216-217 | CHN |
| 102 | OCH3 | H | Cl | H | CO2CH3 | F | H | H | 185-187 | CHN |
| 103 | OCH3 | H | Cl | H | CF3 | H | H | H | 152-156 | CHN |
| 104 | OCH3 | H | Cl | H | CO2CH3 | F | H | CH3 | 175-176(d) | CHN |
| 105 | OCH3 | H | F | H | Cl | Cl | CH3 | H | 236-237(d) | CHN |
| 106 | OCH3 | H | F | H | CO2CH3 | F | H | H | 147-148(d) | CHN |
| 107 | OCH3 | H | F | H | F | F | H | H | 220-221(d) | CHN |
| 108 | OCH3 | H | CF3 | H | Cl | Cl | H | H | 206-207(d) | CHN |
| 109 | OCH3 | H | Br | H | F | H | CH3 | H | 176-178 | CHN |
| 110 | OCH3 | H | Br | H | CO2CH3 | CH3 | H | H | 180-181 | CHN |
| 111 | OC2H5 | H | CH3 | H | NO2 | CH3 | H | H | 235-239 | CHN |
| 112 | OC2H5 | H | H | H | Cl | Cl | H | H | 250-252 | CHN |
| 113 | OC2H5 | H | H | H | Cl | CH3 | H | H | 223-226 | CHN |
| 114 | OC2H5 | H | H | H | CO2CH3 | F | H | H | 173-177 | CHN |
| 115 | OCH3 | H | OCH3 | H | F | F | CH3 | H | 227-229 | CHN |
| 116 | OCH3 | H | OCH3 | H | Cl | Cl | H | H | 188-192(d) | CHN |
| 117 | OC2H5 | H | OCH3 | H | F | F | H | H | 254-256 | CHN |
| 118 | OC2H5 | H | OCH3 | H | CO2CH3 | F | H | H | 186-188 | CHN |
| 119 | OC2H5 | H | OCH3 | H | F | OCH3 | H | H | 195-202 | CHN |
| 120 | OC2H5 | F | H | H | CO2-i-C5H7 | Cl | H | H | 200-202 | CHN |

The term "agriculturally acceptable salts" is employed herein to denote compounds wherein the acidic sulfonamide proton of the compound of Formula I is replaced by a cation which itself is neither herbicidal to crop plants being treated nor significantly deleterious to the applicator, the environment, or the ultimate user of any crop being treated. Suitable cations include, for example, those derived from alkali or alkaline earth metals and those derived from ammonia and amines. Preferred cations include sodium, potassium, magnesium, and aminium cations of the formula

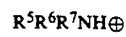

$R^5R^6R^7NH^\oplus$ wherein $R^5$, $R^6$, and $R^7$ each, independently represents hydrogen or $C_1$-$C_{12}$ alkyl, $C_3$-$C_{12}$ cycloalkyl, or $C_3$-$C_{12}$ alkenyl, each of which is optionally substituted by one or more hydroxy, $C_1$-$C_8$ alkoxy, $C_1$-$C_8$ alkylthio or phenyl groups; provided that $R^5$, $R^6$, and $R^7$ are sterically compatible. Additionally, any two of $R^5$, $R^6$, and $R^7$ together may represent an aliphatic difunctional moiety containing 1 to 12 carbon atoms and up to two oxygen or sulfur atoms. Salts of the compounds of Formula I can be prepared by treatment of compounds of Formula I wherein V represents hydrogen with a metal hydroxide, such as sodium hydroxide, potassium hydroxide, or magnesium hydroxide, or an amine, such as ammonia, trimethylamine, hydroxyethylamine, bisallylamine, 2-butoxyethylamine, morpholine, cyclododecylamine, or benzylamine. In the case of metal hydroxides, it is important not to use a large excess of the base as compounds of Formula I are not stable in highly alkaline media. Amounts close to the stoichiometric quantities are preferred.

The compounds of Formula I wherein V represents hydrogen can generally be prepared by combining a 1,2,4-triazolo[1,5-c]pyrimidine-2-sulfonyl halide of Formula 11 with an appropriately substituted N-trialkylsilylaniline of Formula III in the presence of a pyridine compound amine, a tertiary amine or dimethyl sulfoxide catalyst. Excess amine can be employed to react with the hydrohalic acid produced as a by-product. The method is analogous to that described in detail in U.S. Pat. No. 4,910,306 for 1,2,4-triazolo[1,5-a]pyrimidine-2-sulfonamides. The substituents X, Y, and Z of Formula II and A, B, J, and D of Formula III are as defined in the Summary of the Invention. The substituent G of Formula II is chloro or bromo and the substituent R' of Formula III is lower alkyl or benzyl, preferably methyl.

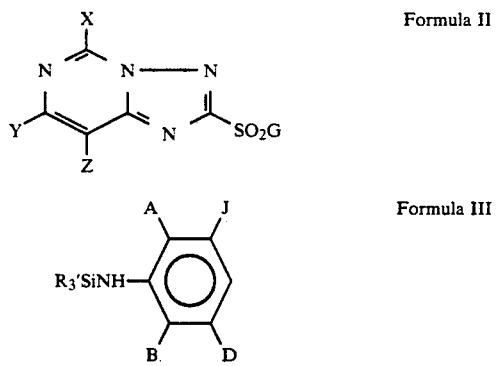

Formula II

Formula III

The preparation is usually accomplished by placing the 1,2,4-triazolo[1,5-c]pyrimidine-2-sulfonyl halide of Formula 11, the N-trialkylsilylaniline of Formula III, the catalyst, and any other solvent employed in a vessel and heating to effect the reaction. After a substantial quantity of the compound of Formula I has formed or a substantial quantity of the sulfonyl halide of Formula II has been consumed, the reaction is allowed to cool and the mixture obtained is contacted with an aqueous reagent: i.e., water or a solution containing water in addition to other components, such as solvents, acids, or bases, that do not cause degradation of compounds of Formula I. The amine hydrohalide salt by-products formed when amine bases are employed as catalysts sometimes precipitate and can be removed by filtration before adding the aqueous reagent. Otherwise, solvents and other volatile components are generally removed by evaporation under reduced pressure and the salt or hydrohalic acid by-product is removed by extraction with water. The crude compounds of Formula I thus obtained can be purified by conventional recovery methods, such as liquid chromatography, paper chromatography, solvent extraction and crystallization from solvents.

Approximately equimolar quantities of the compounds of Formulas II and III are generally used although a substantial excess of one or the other may be employed. It is often advantageous to employ an excess of the N-trialkylsilylaniline.

Most tertiary amine bases such as trialkylamines, and aryl dialkylamines and pyridine bases such as pyridine, picolines, and lutidines, are useful as catalysts in the reaction. Pyridine is preferred. The amine base can be used in approximately equimolar quantities with the compounds of Formula II or in excess. It is sometimes preferred to use a large excess. Dimethyl sulfoxide, which is generally the most preferred catalyst, is however, typically used in less than an equimolar amount. Amounts over about 0.5 molar equivalent are deleterious. If desired, a solvent which is unreactive toward the reagents and in which the reagents are soluble can be used. Suitable solvents include acetonitrile, dimethylformamide, toluene, and the like. Acetonitrile is often preferred.

The reaction mixture is heated at a sufficiently high temperature and for a sufficient period of time to effect the reaction. Generally, temperatures of about 10° C. to about 150° C. are employed. Temperatures of about 30° C. to about 100° C. are preferred. Times up to about 72 hours are typical and times of from about 12 hours to about 48 hours are preferred. It is further preferred to carry out the reaction with stirring and in a vessel equipped with means to exclude moisture from the system.

It is often convenient to prepare the required N-trialkylsilylaniline of Formula III from an appropriate aniline and a trialkylsilyl chloride and use the freshly prepared product directly in the process. Typically, excess trialkylsilyl chloride is added to a slurry of sodium iodide in acetonitrile, the appropriate aniline and triethylamine are added, and after stirring for several hours ether is added. The mixture is filtered and the volatile components removed by evaporation under reduced pressure leaving the N-trialkylsilylaniline as a residue which can be used directly.

Compounds of Formula I can be made in a more straightforward way by allowing sulfonyl chlorides of Formula II to react with appropriately substituted anilines in an inert solvent, such as acetonitrile, in the presence of pyridine or a methylpyridine and a catalytic amount of dimethyl sulfoxide. The reaction typically takes place well at temperatures between about 0° C. and 60° C. and is conveniently carried out at ambient temperatures. Generally, an equimolar amount or up to a 100 percent excess of substituted aniline and of pyridine or methylpyridine and a catalytic amount of about 0.05 to about 0.30 moles of dimethyl sulfoxide are employed per mole of sulfonyl halide. The compound of Formula I prepared can be recovered by conventional techniques.

Compounds of Formula I wherein V represents hydrogen and X and/or Y represents $SCH_3$ or OR, can be made from the corresponding compound of Formula I wherein X and/or Y represents Cl by treatment with an appropriate nucleophilic reagent, such as sodium methoxide or sodium methanethiolate in methanol. The reaction conditions employed are similar to those used for the related exchange reactions of 2- and 4-chloropyrimidines. Non-aqueous media are preferred. Selective replacement of chlorine in the X position can readily be achieved as this chlorine is much more reactive than the chlorine in the Y position.

Compounds of Formula I wherein V represents $C(O)R^3$ can be prepared from compounds of Formula I wherein V represents hydrogen by acylation with a compound of the formula $R^3C(O)Cl$ using conventional procedures known in the art for the acylation of sulfonamides.

The 1,2,4-triazolo[1,5-c]pyrimidine-2-sulfonyl halides of Formula II can be prepared by treatment of compounds of Formula IV, wherein R" represents hydrogen, benzyl, or $C_2$-$C_4$ alkyl, and X, Y, and Z are as defined in the Summary of the Invention, except that X may not be $SCH_3$, with chlorine in aqueous chloroform or aqueous acetic acid. The procedures used are well known in the art and have been applied to certain compounds related to the compounds of Formula II but with different substituents, for example, in British Patent 951,652.

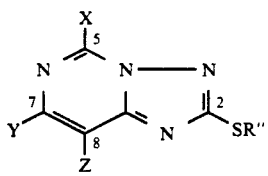

Formula IV

Many of the 1,2,4-triazolo[1,5-c]pyrimidine compounds of Formula IV that are useful as intermediates in the preparation of compounds of Formula II are known in the art and general methods for their preparation are known as well. Thus, for example, many 4-hydrazinopyrimidines, optionally substituted in the 2, 5, and 6 positions are known to react with carbon disulfide and an alkali metal hydroxide in an alcoholic solvent to produce compounds of Formula IV wherein R" represents hydrogen. Procedures are given in the *Australian Journal of Chemistry*, 32, 2713-2726 (1979) and elsewhere. Trialkylamines can often be employed in place of the alkali metal alkoxide. This reaction involves an unusual rearrangement, but the positions of the substituents in the compound of Formula IV produced can be predicted by comparing the substituents of Formula V with the substituent of the same letter designation of Formula IV.

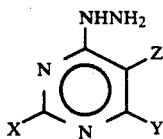

Formula V

Compounds of Formula IV wherein R" represents benzyl or $C_2$-$C_4$ alkyl can be prepared from the corresponding compound wherein R" represents hydrogen by alkylation with an appropriate alkylating agent, such as benzyl chloride, ethyl bromide, propyl methanesulfonate, and the like. The reaction is generally carried out using standard conditions known in the art for the alkylation of mercaptans. Generally, a base, such as an alkali metal alkoxide or a tertiary amine is employed. It is often preferred to do the alkylation on a compound of Formula IV wherein R" represents hydrogen prepared as described above without recovery.

4-Hydrazinopyrimidines having a methoxy substituent in the 2-position, however, do not yield 5-methoxy substituted compounds of Formula IV (X represents methoxy) in the above process; 5-hydroxy compounds are formed instead. In order to obtain 5-methoxy compounds of Formula IV, it is possible to convert 5-hydroxy compounds to 5-chloro compounds by treatment with phosphorus oxychloride and then to prepare the desired 5-methoxy compounds by treatment of the 5-chloro compounds obtained with sodium methoxide in the methanol.

When a trialkylamine, such as triethylamine, is employed as the base in the reaction of a compound of Formula V with carbon disulfide and benzyl chloride, the unusual rearrangement described above takes place more slowly and it is usually possible to recover an unrearranged 1,2,4-triazolo[4,3-c]pyrimidine compound of Formula VI as the product.

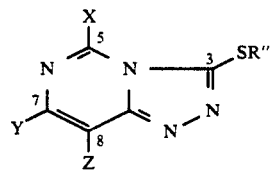

Formula VI

Often mixtures of the compounds of Formula IV and VI are obtained. Compounds of Formula VI can be converted to compounds of Formula IV by treatment with an alkali metal alkoxide. The reaction is usually carried out in an alcohol solvent and the mixture is usually heated. Compounds of Formula IV and VI can be distinguished by their uv spectra in the 200-280 nanometer range, compounds of Formula IV having a characteristic strong absorption below 250 nanometers (see *J. Chem. Soc.* 1963, 5642-5659). The compounds of Formula VI also have a relatively short retention time on reverse phase high pressure liquid chromatography.

It is further possible, and in many instances preferable, to prepare compounds of Formula IV wherein X represents OR and R" represents an allowable moiety other than hydrogen by first preparing a compound of either Formula IV or Formula VI wherein X represents $C_1$-$C_4$ alkylthio, preferably methylthio, from a compound of Formula V wherein X represents $C_1$-$C_4$ alkylthio and subsequently exchanging the alkylthio with an OR moiety and, in the case of compounds of Formula VI, rearranging the heterocycle. The desired reaction can be accomplished by treating the compound of Formula IV or VI wherein X represents $C_1$-$C_4$ alkylthio with an alkali metal $C_1$-$C_3$ alkoxide in a medium containing the corresponding alcohol and in the presence of a carbonyl or cyano substituted vinyl compound which is reactive with $C_1$-$C_4$ alkanethiols. The last named reagent, which includes compounds such as dialkyl maleates, methyl vinyl ketone, methyl and ethyl acrylate, and acrylonitrile, is present to react with the alkanethiol produced as a by-product and remove it from the solution.

Conditions conducive to the desired reaction are employed. The starting compound of Formula IV and carbonyl or cyano substituted vinyl compound are typically employed in approximately equimolar quantities. The alkali metal alkoxide, on the other hand, is generally employed in catalytic amounts ranging from about 5 to about 30 mole percent of the starting compound of Formula IV or VI. The reaction is best conducted at temperatures from about 0° C. to the boiling point of the alcohol solvent and is complete in about 10 minutes to about 4 hours. The desired product of Formula IV wherein X represents OR can be recovered by neutralizing the catalyst with an acid, such as acetic acid, and then removing the solvent and any volatiles by evaporation or adding water and collecting the insolubles. Further purification can be achieved by conventional means, such as dissolving in methylene chloride or another water-immiscible solvent, extracting with water, and removing the solvent by evaporation. The final products are solids which are often recrystallizable from solvents such as hexane and ethanol.

The compounds of Formula IV wherein R" represents benzyl or $C_2$-$C_4$ alkyl, X represents OR (R defined as before), and Y and Z independently represent OR, H, $CH_3$, $CF_3$, Cl, Br, or F are novel, useful intermediates.

Additional methods for the preparation of the compounds of Formulas I, II, and IV will be apparent to those skilled in the art.

The N-trialkylsilylanilines of Formula III are known in the art or can be prepared by methods given in U.S. Pat. No. 4,910,306 from anilines that are known in the art, including U.S. Pat. No. 4,886,883.

The substituted 6- (or 4-)hydrazinopyrimidines employed as starting materials or suitable methods for the preparation of these compounds and the required starting materials for those methods are known in the art. Generally, hydrazinopyrimidines are prepared by allowing a substituted 6-(or 4-)halopyrimidine to react with excess hydrazine or approximately equimolar hydrazine and a base, such as potassium carbonate or sodium bicarbonate. The reaction method is analogous to the related amination reaction, which is very well known. Much of this art is summarized in the monograph, *The Pyrimidines*, by D.J. Brown, from the series, *The Chemistry of Heterocyclic Compounds*, edited by Weissberger and Taylor.

While it is possible to utilize the 1,2,4-triazolo[1,5-c]pyrimidine-2-sulfonamide compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface active agents include salts of alkyl sulfates, such as diethanolammonium lauryl sulfate: alkylarylsulfonate salts, such as calcium dodecylbenzenesulfonate: alkylphenol-alkylene oxide products, such as nonylphenol-$C_{18}$ ethoxylate; alcohol-alkylene oxide addition products, such as tridecyl alcohol-$C_{16}$ ethoxylate: soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate: sorbitol esters, such as sorbitol oleate: quaternary amines, such as lauryl trimethylammonium chloride: polyethylene glycol esters of fatty acids, such as polyethylene glycol stearate: block copolymers of ethylene oxide and propylene oxide: and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorants, penetration aids, spreading agents, sticking agents, dispersing agents, thickening agents, freeze point depressants, antimicrobial agents, and the like. The compositions can also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a from about 5 to about 98 weight percent, preferably about 10 to about 90 weight percent. Such compositions are typically diluted with an inert carrier, such as water, before application. The diluted compositions usually applied to weeds or the locus of weeds generally contain about 0.001 to about 5 weight percent active ingredient and preferably contain about 0.01 to about 0.5 percent.

The present compositions can be applied to weeds or their locus by the use of conventional ground or aerial dusters and sprayers, by addition to irrigation water, and by other conventional means known to those skilled in the art.

The compounds of Formula I have been found to be useful preemergence and postemergence herbicides. Some of the compounds are useful for the selective control of broadleaf plants and nutsedge in grass crops, such as corn, wheat, barley, and rice, and are especially useful in the selective control of broadleaf weeds in wheat and corn. Others can be used to control broadleaf weeds in soybeans. Examples of the types of broadleaf weeds controlled include various species of prickly sida, morning glory, cocklebur, jimsonweed, velvet leaf, pigweed and black nightshade. Certain grassy weeds, such as crabgrass and yellow foxtail are also often controlled. As will be appreciated by those skilled in the art, not all of the compounds control all of the weeds or are selective for all of the crops.

The term herbicide is used herein to mean an active ingredient which controls or adversely modifies growth of plants. An herbicidally effective or vegetation controlling amount is an amount of active ingredient which causes an adversely modifying effect and includes deviations from natural development, killing, regulation, dessication, retardation, and the like. The terms plants and vegetation are meant to include germinant seeds, emerging seedlings and established vegetation.

Herbicidal activity is exhibited by the compounds of the present invention when they are applied directly to the plant or to the locus of the plant at any stage of growth or before emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote selective herbicidal action. Generally, it is preferred to apply the compounds of Formula I postemergence to relatively immature plants to achieve the maximum control of broadleaf weeds. It is also preferred to employ the compounds under conditions such that broadleaf weeds are controlled in the presence of a wheat crop.

Application rates of about 0.001 to about 10 Kg/Ha are generally employed in postemergence operations: for preemergence applications, rates of about 0.01 to about 10 Kg/Ha are generally employed.

EXAMPLES

The following Examples are presented to illustrate the various aspects of this invention and should not be construed as limitations to the claims.

The proton nuclear magnetic resonance and infrared spectra of each of the compounds prepared was found to be compatible with the structure assigned. High pressure liquid chromatography (HPLC) was done using a Waters Associates, Inc. chromatograph equipped with a $\mu$ Bondapac C-18 column and eluting with a 60:40 mixture of water and acetonitrile containing 0.5 percent acetic acid. Components were monitored with a uv detector at 254 nm. Gas chromatography (GLC) was done using a Hewlett-Packard 5830-A chromatograph equipped with a thermal conductivity detector and a glass column filled with 5 percent DC-410 on 60×80 mesh GasChromQ. Melting points were determined with a Thomas-Hoover capillary melting point apparatus.

EXAMPLE 1

Preparation of 4,5-Dichloro-6-methoxy-2-methylpyrimidine

A solution containing 38 g (0.17 mol) of 2-methyl-4,5,6-trichloropyrimidine in 200 ml of methanol was cooled in an ice bath to 10'-15° C. and sodium methoxide as a 25 percent solution in methanol was added slowly with stirring until the starting pyrimidine could no longer be detected by GLC analysis. Water was then added and the resulting mixture was extracted with methylene chloride. Removal of the solvent and other volatiles from the extract by evaporation under reduced pressure left the title compound as a white powder melting at 77°-78° C.

EXAMPLE 2

Preparation of 4,6-Difluoro-2-methylthiopyrimidine

A slurry of 21.9 g (0.377 mol) of potassium fluoride in 200 ml of N-methylpyrrolidone was prepared in a reaction flask and heated to distill out any moisture. When the head temperature reached 200° C. the mixture was cooled to about 85° C. and 24.5 g (0.126 mol) of 4,6-dichloro-2-methylthiopyrimidine was added with stirring The mixture was then heated with stirring at about 144° C. under a reduced pressure of about 150 mmHg, slowly removing the solvent and the title compound product by distillation. This was continued until very little liquid remained in the flask. The distillate and the residue were combined and diluted with ether and the resulting mixture was extracted with water several times. The remaining ethereal solution was dried over magnesium sulfate and concentrated under reduced pressure to obtain a residue. This was distilled and the fraction boiling at about 127° C. at 150 mmHg pressure was collected to obtain 16.1 g of the title compound as white crystals melting at 31°-32° C.

EXAMPLE 3

Preparation of 4,6-Dibromo-2-methylthiopyrimidine

A mixture of 20.0 g (0.126 mol) of 4,6-dihydroxy-2-methylthiopyrimidine, 150 g (0.523 mol) of phosphorus oxybromide, and 600 ml of acetonitrile was prepared and heated at reflux with stirring for 3 hours. The solids intially tended to dissolve, but later more solids began to form. The volatiles were removed by evaporation under reduced pressure and the residue was diluted with methylene chloride and then cautiously with water. The aqueous layer was removed and the organic layer was extracted with water several times, dried over magnesium sulfate, and concentrated under reduced pressure. The residue was dissolved in hexane and the resulting solution dried over magnesium sulfate and concentrated under reduced pressure to obtain 26.8 g of the title compound as a white powder melting at 82°-84° C.

EXAMPLE 4

Preparation of 5-Chloro-4-methoxy-2-methyl-6-hydrazinopyrimidine 4,5-Dichloro-6-methoxy-2-methylpyrimidine (21 g, 0.11 mol), 25 ml of hydrazine hydrate, and 25 ml of water were combined and heated to reflux for 25 min. The mixture was then cooled and extracted with methylene chloride. The extract was washed with water, dried over magnesium sulfate, and concentrated under reduced pressure. The solid residue was extracted with hexane and dried to obtain 12.8 g (62 percent of theory) of the title compound as a fluffy white solid melting at 158°–159° C.

The following compounds were prepared similarly, adjusting the reaction temperature appropriately:

4-bromo-2-methylthio-6-hydrazinopyrimidine, off-white powder, melting at 153°–154° C.;

4-methyl-2-methylthio-6-hydrazinopyrimidine, white powder, melting at 136°–137° C.;

5-chloro-2-methylthio-4-hydrazinopyrimidine, white powder, melting at 154°–155° C.; and 2-methylthio-4-hydrazinopyrimidine, tan powder, melting at 138°–139° C.

EXAMPLE 5

Preparation of
4-Fluoro-2-methylthio-6-hydrazinopyrimidine

A solution of 15.8 g (0.097 mol) of 4,6-di-fluoro-2-methylthiopyrimidine in 50 ml of ethanol was added slowly with stirring to a solution of 11.6 ml (12.0 g, 0.214 mol) of hydrazine monohydrate in 100 ml of ethanol, keeping the temperature below 0° C. by external cooling. The mixture was allowed to react for an additional 30 min and the volatiles were then removed by evaporation under reduced pressure. The residue was diluted with ethyl acetate and the resulting solution extracted with water, dried over magnesium sulfate, and concentrated under reduced pressure to obtain 16.0 g of the title compound as a white powder melting at 153°–154° C.

Elemental Analysis for $C_5H_7FN_4S$:
Calculated: %C, 34.5: %H, 4.05; %N, 32.2.
Found: %C, 34.5; %H, 3.94: %N, 32.2.

EXAMPLE 6

Preparation of
4-Chloro-2-methylthio-5-methoxy-6-hydrazinopyrimidine

A mixture of 48.1 g (0.21 mol) of 4,6-di-chloro-2-methylthio-5-methoxypyrimidine, 29.5 g (0.21 mol) of potassium carbonate, 80 ml of hydrazine monohydrate, and 80 ml of water was prepared and heated at reflux with stirring for about 30 min at which time the reaction appeared by high pressure liquid chromatography to be complete. The mixture was allowed to cool and was extracted with methylene chloride. The extract was dried over magnesium sulfate and concentrated under reduced pressure. The residue was mixed with hexane and the solids removed by filtration and dried to obtain 34.7 g of the title compound as a tan solid melting at 118°–119° C.

EXAMPLE 7

Preparation of
2-Benzylthio-8-chloro-7-methoxy-5-methyl-1,2,4-triazolo[1,5-c]pyrimidine 5-Chloro-4-methoxy-2-methyl-6-hydrazinopyrimidine (11.3 g, 0.060 mol), 13.7 g (0.18 mol) of carbon disulfide, 15.6 g (0.072 mol) of sodium methoxide as a 25 percent solution in methanol and 250 ml of ethanol were combined, stirred at ambient temperature for about 1 hour, and then heated at reflux for 2 hours at which time the reaction appeared to be complete by HPLC analysis. Benzyl chloride (9.1 g, 0.072 mol) was then added with continued refluxing and stirring. A solid separated immediately. Additional small quantities of sodium methoxide and benzyl chloride were added until HPLC analysis indicated complete benzylation had taken place. The mixture was allowed to cool and 10 ml of acetic acid was added. The resulting mixture was diluted to about 1 liter with water and extracted with methylene chloride. The extract was washed with water, dried over magnesium sulfate, and concentrated under reduced pressure. The residue from the evaporation was triturated with hexane, filtered, and dried. It was then recrystallized from methanol to obtain 16.3 g (85 percent of theory) of the title compound as an off-white powder melting at 115°–116° C.

Elemental Analysis for $C_{14}H_{13}ClN_4OS$:
Calculated: %C, 52.4; %H, 4.08: %N, 17.47.
Found: %C, 52.3; %H, 4.04; %N, 17.14.

EXAMPLE 8

Preparation of
3-Benzylthio-7-fluoro-5-methylthio-1,2,4-triazolo[4,3-c]pyrimidine 4-Fluoro-2-methylthio-6-hydrazinopyrimidine (15.0 g, 0.086 mol), 15.5 ml (19.7 g, 0.258 mol) of carbon disulfide, 48 ml (34.8 g, 0.344 mol) of triethylamine, and 400 ml of ethanol were combined with stirring and after 15 min heated to reflux with stirring for 2.5 hours. The resulting mixture was allowed to cool to ambient temperature and then 16.4 g (0.129 mol) of benzyl chloride was added with stirring and allowed to react for 3 hours. The volatiles were removed by evaporation under reduced pressure and the residue was dissolved in methylene chloride. The resulting solution was extracted with water, dried over magnesium sulfate and concentrated under reduced pressure. The residue was triturated with hexane and filtered to obtain 20.9 g of the title compound as a yellow-orange powder melting at 74°–77° C. There was also a small amount of 2-benzylthio-7-fluoro-5-methylthio-1,2,4-triazolo[1,5-c]pyrimidine present. The nmr and uv spectra were consistent with the assigned structure and the presence of the impurity.

The following compounds were prepared similarly and the products found to have nmr and uv spectra consistent with the assigned structures:

3-benzylthio-7-chloro-5-methylthio-1,2,4-triazolo[4,3-c]pyrimidine, pale yellow powder melting at 131°–132° C.;

3-benzylthio-7-methyl-5-methylthio-1,2,4-triazolo[4,3-cpyrimidine, pale yellow powder melting at 138°–139° C.;

3-benzylthio-7-bromo-5-methylthio-1,2,4-triazolo[4,3-c]pyrimidine, tan powder melting at 125°–127° C.;

3-benzylthio-5-methylthio-1,2,4-triazolo[4,3-cpyrimidine, off-white powder melting at 108°–109° C.; and 3-benzylthio-8-chloro-5-methylthio-1,2,4-triazolo[4,3-cpyrimidine, viscous red oil containing a considerable amount of the 1,5-c isomer which melted at 103°–106° C. (isolated independently).

EXAMPLE 9

Preparation of
2-Benzylthio-7-fluoro-5-methoxy-1,2,4-triazolo[1,5-c]pyrimidine

A 25 percent solution of sodium methoxide in methanol (1.9 ml, 0.0085 mol) was added to a solution of 19.9 g (0.065 mol) of 3-benzylthio-7-fluoro-5-methylthio-1,2,4-triazolo[4,3-c]pyrimidine containing a small amount of 2-benzylthio-7-fluoro-5-methylthio-1,2,4- triazolo[1,5-c]pyrimidine and 11.2 g (0.065 mol) of diethyl maleate in 250 ml of ethanol at ambient temperature with stirring and allowed to react for about 1 hour. Acetic acid (4 ml) was then added and the volatiles were removed by evaporation under reduced pressure. The residue was dissolved in methylene chloride and the resulting solution was extracted with water, dried over magnesium sulfate, and concentrated by evaporation under reduced pressure. The residue was triturated with hexane, filtered, and dried to obtain 10.7 g of the title compound as a white powder melting at 121°–122° C. The nmr and uv spectra were consistent with the assigned structure.

The following compounds were prepared similarly and the products found to have nmr and uv spectra consistent with the assigned structures:

2-benzylthio-7-chloro-5-methoxy-1,2,4-triazolo[1,5-c]pyrimidine, off-white powder melting at 121°–122° C. having a consistent CHN analysis;
2-benzylthio-7-chloro-5-ethoxy-1,2,4-triazolo[1,5-c]pyrimidine, white powder melting at 85°–86° C.;
2-benzylthio-7-methyl-5-methoxy-1,2,4-triazolo[1,5-c]pyrimidine, white powder melting at 93°–94° C.;
2-benzylthio-7-methyl-5-ethoxy-1,2,4-triazolo[1,5-c]pyrimidine, white powder melting at 77°–78° C.;
2-benzylthio-5-methoxy-1,2,4-triazolo[1,5-c]pyrimidine, light tan powder melting at 96°–97° C.;
2-benzylthio-8-chloro-5-methoxy-1,2,4-triazolo[1,5-c]pyrimidine, pale yellow powder melting at 109°–110° C. (made from either isomer):
2-benzylthio-7-chloro-5,8-dimethoxy-1,2,4-triazolo[1,5-c]pyrimidine, light tan powder melting at 94°–95° C.;
2-benzylthio-5,8-dimethoxy-1,2,4-triazolo[1,5-c]pyrimidine, white powder melting at 117°–119° C.;
2-benzylthio-5-ethoxy-1,2,4-triazolo[1,5-c]pyrimidine, white powder melting at 64°–66° C.;
2-benzylthio-8-methyl-5-methoxy-1,2,4-triazolo[1,5-c]pyrimidine, white powder melting at 82°–84° C.;
2-benzylthio-8-methyl-5-ethoxy-1,2,4-triazolo[1,5-c]pyrimidine, white powder;
2-benzylthio-7-ethyl-5-methoxy-1,2,4-triazolo[1,5-c]pyrimidine, off-white powder melting at 76°–77° C.;
2-benzylthio-8-chloro-5-ethoxy-1,2,4-triazolo[1,5-c]pyrimidine, white powder melting at 112°–115° C.;
2-benzylthio-8-fluoro-5-methoxy-1,2,4-triazolo[1,5-c]pyrimidine, white powder melting at 113°–115° C.;
2-benzylthio-7-bromo-5-methoxy-1,2,4-triazolo[1,5-c]pyrimidine, tan powder melting at 125°–126° C.;
2-benzylthio-8-bromo-5-methoxy-1,2,4-triazolo[1,5-c]pyrimidine, tan powder melting at 120°–124° C.;
2-benzylthio-5-methoxy-7-(trifluoromethyl)1,2,4-triazolo[1,5-c]pyrimidine, pale yellow powder melting at 113°–114° C.;
2-benzylthio-5-methoxy-8-(trifluoromethyl)1,2,4-triazolo[1,5-c]pyrimidine, tan powder melting at 107°–108° C.;
2-benzylthio-5-ethoxy-8-methoxy-1,2,4-triazolo[1,5-c]pyrimidine, white powder melting at 82°–84° C.;
2-benzylthio-7,8-dichloro-5-methoxy-1,2,4-triazolo[1,5-c]pyrimidine, yellow powder melting at 116°–118° C.;
2-benzylthio-7,8-dichloro-5-ethoxy-1,2,4-triazolo[1,5-c]pyrimidine, yellow powder melting at 118°–120° C.;
2-benzylthio-8-bromo-5,7-dimethoxy-1,2,4-triazolo[1,5-c]pyrimidine, tan powder melting at 124°–125° C.; and
2-benzylthio-8-chloro-7-methyl-5-methoxy-1,2,4-triazolo[1,5-c]pyrimidine, white powder melting at 97°–98° C.

EXAMPLE 10

Preparation of 5-Chloro-7-methoxy-2-benzylthio-1,2,4-triazolo[1,5-c]pyrimidine 2,4-Dimethoxy-6-hydrazinopyrimidine (48.4 g, 0.28 mol), 121.6 g (1.6 mol) of carbon disulfide, 145.2 g (1.44 mol) of triethylamine, and 2 l of ethanol were combined with stirring and after 30 min heated at reflux for 2 hours. Benzyl chloride (40.4 g, 0.32 mol) was added and refluxing continued for another hour. The mixture was concentrated under reduced pressure and the residue was combined with 800 ml of acetonitrile and 250 ml of phosphorus oxychloride. The mixture was heated at reflux with stirring for 3 hours. It was then concentrated under reduced pressure and the residue poured onto a mixture of ice and methylene chloride. The organic phase was separated, filtered through silica gel, and concentrated under reduced pressure. The residue was extracted with hot hexane and the hexane then removed evaporation. This fraction was purified by preparative HPLC to obtain about 5 g of the title compound. The hexane insolubles were dissolved in hot carbon tetrachloride. Filtration and evaporation of the carbon tetrachloride left an oil which solidified when a small amount of acetone was added. This was combined with the previously isolated product and extracted with hot hexane again. The residue was dried to obtain 31.2 g (36 percent of theory) of the title compound as a pale yellow powder of about 95 percent purity. A further HPLC purified sample melted at 140°–141° C.

Elemental Analysis for $C_{13}H_{11}ClN_4OS$:
Calculated: %C, 50.89; %H, 3.61; %N, 18.26.
Found: %C, 50.00; %H, 3.62; %N, 18.44.

The compound 8-bromo-5-chloro-7-methoxy-2-benzylthio-1,2,4-triazolo[1,5-c]pyrimidine was prepared similarly and found to have a satisfactory elemental analysis and a melting point of 124°–125° C.

EXAMPLE 11

Preparation of 8-Chloro-2-chlorosulfonyl-7-methoxy-5-methyl-1,2,4-triazolo[1,5-c]pyrimidine 2-Benzylthio-8-chloro-7-methoxy-5-methyl-1,2,4-triazolo[1,5-c]pyrimidine (2.0 g, 0.0060 mol) 50 ml of chloroform and 50 ml of water were combined and the mixture cooled with an ice bath. Chlorine gas (4.4 g, 0.060 mol) was added slowly with stirring keeping the temperature below about 10° C. The mixture was stirred another 30 min and then the aqueous layer was removed and the organic layer was dried over sodium sulfate and concentrated under reduced pressure. The residue was triturated with hexane to obtain a solid product which was recovered by filtration and dried to obtain 1.6 g (90 percent of theory) of the title compound as a white powder melting at 100°–101° C.

The following compounds were prepared similarly and the products found to have nmr spectra consistent with the assigned structures:

8-chloro-2-chlorosulfonyl-5-methoxy-1,2,4-triazolo[1,5-c]pyrimidine, white powder melting at 122°–124° C.;
2-chlorosulfonyl-7-fluoro-5-methoxy-1,2,4-triazolo[1,5-c]pyrimidine, white powder melting at 106°–107° C.;

7-chloro-2-chlorosulfonyl-5,8-dimethoxy-1,2,4-triazolo[1,5-c]pyrimidine, pale yellow powder melting at 132°-133° C.;

2-chlorosulfonyl-5-methoxy-1,2,4-triazolo[1,5-c]pyrimidine, white powder melting at 128°-129° C.;

7-chloro-2-chlorosulfonyl-5-methoxy-1,2,4-triazolo[1,5-c]pyrimidine, pale yellow powder melting at 136°-137° C.;

7-chloro-2-chlorosulfonyl-5-ethoxy-1,2,4-triazolo[1,5-c]pyrimidine, white powder melting at 99°-101° C.;

2-chlorosulfonyl-5-methoxy-7-methyl-1,2,4-triazolo[1,5-c]pyrimidine, white powder melting at 139°-141° C.;

2-chlorosulfonyl-5-ethoxy-7-methyl-1,2,4-triazolo[1,5-c]pyrimidine, white powder melting at 104°-106° C.;

2-chlorosulfonyl-5-ethoxy-1,2,4-triazolo[1,5-c]pyrimidine, white powder;

2-chlorosulfonyl-5-methoxy-8-methyl-1,2,4-triazolo[1,5-c]pyrimidine, pale yellow powder melting at 124°-126° C.;

2-chlorosulfonyl-5-ethoxy-8-methyl-1,2,4-triazolo[1,5-c]pyrimidine, white powder;

2-chlorosulfonyl-5-methoxy-7-ethyl-1,2,4-triazolo[1,5-c]pyrimidine, white powder melting at 101°-103° C.;

8-chloro-2-chlorosulfonyl-5-ethoxy-1,2,4-triazolo[1,5-c]pyrimidine, white powder melting at 103°-105° C.;

2-chlorosulfonyl-5-ethoxy-7-fluoro-1,2,4-triazolo[1,5-c]pyrimidine, white powder melting at 80°-81° C.;

2-chlorosulfonyl-8-fluoro-5-methoxy-1,2,4-triazolo[1,5-c]pyrimidine, white powder melting at 78°-80° C.;

7-bromo-2-chlorosulfonyl-5-methoxy-1,2,4-triazolo[1,5-c]pyrimidine, orange powder melting at 148°-150° C.;

8-bromo-2-chlorosulfonyl-5-methoxy-1,2,4-triazolo[1,5-c]pyrimidine, light yellow powder melting at 130°-132° C.;

2-chlorosulfonyl-5-methoxy-7-(trifluoromethyl)-1,2,4-triazolo[1,5-c]pyrimidine, tan powder melting at 89°-90° C.;

2-chlorosulfonyl-5-methoxy-8-(trifluoromethyl)-1,2,4-triazolo[1,5-c]pyrimidine, yellow powder melting at 110°-112° C.;

2-chlorosulfonyl-5-ethoxy-8-methoxy-1,2,4-triazolo[1,5-c]pyrimidine, white powder;

2-chlorosulfonyl-7,8-dichloro-5-methoxy-1,2,4-triazolo[1,5-c]pyrimidine, yellow powder melting at 91°-93° C.;

2-chlorosulfonyl-7,8-dichloro-5-ethoxy-1,2,4-triazolo[1,5-c]pyrimidine, yellow powder melting at 89°-92° C.;

2-chlorosulfonyl-8-bromo-5,7-dimethoxy-1,2,4-triazolo[1,5-c]pyrimidine, white powder melting at 164°-166° C.; and 2-chlorosulfonyl-8-chloro-5-methoxy-7-methyl-1,2,4-triazolo[1,5-c]pyrimidine, white powder melting at 110°-111° C.

EXAMPLE 12

Preparation of 5-Chloro-7-methoxy-2-chlorosulfonyl-1,2,4-triazolo[1,5-c]pyrimidine 5-Chloro-7-methoxy-2-benzylthio-1,2,4-triazolo[1,5-c]pyrimidine (10.0 g, 0.033 mol), 200 ml of chloroform, and 200 ml of water were combined and cooled with an ice bath. Chlorine gas (10.2 g, 0.143 mol) was added slowly with stirring so that the temperature remained below about 3° C. and stirring was continued for another 30 min. The organic phase was separated, dried over magnesium sulfate, and concentrated under reduced pressure to obtain 9.1 g (97 percent of theory) of the title compound as a yellow semisolid. A small portion was purified by trituration with ether to obtain a white powder melting at 79°-80° C.

The following compound was prepared in the same manner:

8-bromo-5-chloro-7-methoxy-2-chlorosulfonyl-1,2,4-triazolo[1,5-c]pyrimidine: m.p., 164°-166° C.

EXAMPLE 13

Preparation of N-(2,6-Dichlorophenyl)-8-chloro-7-methoxy-5-methyl-1,2,4-triazolo[1,5-c]pyrimidine-2-sulfonamide Anhydrous sodium iodide (11.7 g, 0.078 mol) was placed in 50 ml of dry acetonitrile and 8.5 g (0.078 mol) of trimethylsilyl chloride added with stirring. To this was added 6.3 g (0.039 mol) of 2,6-dichloroaniline and 7.9 g (0.078 mol) of triethylamine. The mixture was stirred at ambient temperature for 30 min and then the volatiles were carefully removed by evaporation under reduced pressure and the residue diluted with ether and filtered. The contents of this solution appeared to be N-trimethylsilyl-2,6-dichloroaniline of about 97 percent purity by GLC analysis. The ether precipitation of insolubles was repeated and the ether was removed by evaporation under reduced pressure. The residue was mixed with 50 ml of dry acetonitrile, 3.9 g (0.013 mol) of 8-chloro-2-chlorosulfonyl-7-methoxy-5-methyl-1,2,4-triazolo[1,5-c]pyrimidine, and 0.2 ml (0.003 mol) of dimethylsulfoxide and the mixture stirred overnight. The resulting mixture was concentrated under reduced pressure and the solid residue was mixed with hexane and water and filtered. The residue was then dissolved in 400 ml of methylene chloride and resulting solution was twice extracted with water, dried over sodium sulfate and filtered. It was then concentrated under reduced pressure and the residue was mixed with hexane, collected by filtration, and dried to obtain 3.3 g (60 percent of theory) of the title compound as a pale yellow powder melting at 255°-256° C. with decomposition.

Elemental Analysis for $C_{17}H_{10}Cl_3N_5O_3S$:
Calculated: %C, 36.94; %H, 2.38; %N, 16.57.
Found: %C, 36.98; %H, 2.41; %N, 16.30.

The following compounds and the other compounds in Table I for which properties are given were prepared by the same method and found to have satisfactory elemental (CHN) analyses and to have nmr spectra consistent with the assigned structures:

N-(2,6-dichlorophenyl)-5-chloro-7-methoxy-1,2,4-triazolo[1,5-c]pyrimidine-2-sulfonamide; off-white powder;

N-(2,6-dichloro-3-methylphenyl)-5-chloro-7-methoxy-1,2,4-triazolo[1,5-c]pyrimidine-2-sulfonamide; m.p , 204°-205° C.;

N-(2,6-dichlorophenyl)-8-bromo-5-chloro-7-methoxy-1,2,4-triazolo[1,5-c]pyrimidine-2-sulfonamide; powder;

N-(2,6-dichloro-3-methylphenyl)-8-bromo-5-chloro-7-methoxy-1,2,4-triazolo[1,5-c]pyrimidine-2-sulfonamide; tan powder; and N-(2,6-dichloro-3-methylphenyl)-8-chloro-7-methoxy-5-methyl-1,2,4-triazolo[1,5-c]pyrimidine-2-sulfonamide; m.p., 231°-232° C.

EXAMPLE 14

Preparation of
N-(2,6-Dichlorophenyl)-5,7-dimethoxy-1,2,4-triazolo[1,5-c]pyrimidine-2-sulfonamide N-(2,6-Dichlorophenyl)-5-chloro-7-methoxy-1,2,4-triazolo[1,5-c]pyrimidine-2-sulfonamide (0.8 g, 0.002 mol) was mixed with 25 ml of methanol and 1.34 ml of 25 percent sodium methoxide in methanol (0.006 mol) added with stirring. After 10 min 2 ml of acetic acid was added and the mixture was concentrated under reduced pressure. The residue was dissolved in methylene chloride and the solution extracted with water, dried over sodium sulfate, and concentrated under reduced pressure. The residue was mixed with carbon tetrachloride, collected by filtration, and dried to obtain 0.5 g of the title compound as an off-white powder melting at 211°-212° C.

Elemental Analysis for $C_{13}H_{11}Cl_2N_5O_4S$:
Calculated: %C, 38.62; %H, 2.74; %N, 17.33.
Found: %C, 38.09; %H, 2.82; %N, 17.18.

The following compounds were prepared by similar procedures and found to have satisfactory elemental analyses and nmr spectra:
N-(2,6-dichloro-3-methylphenyl)-5,7-dimethoxy-1,2,4-triazolo[1,5-c]pyrimidine-2-sulfonamide: m.p., 212°-213° C.;
N-(2,6-dichlorophenyl)-8-bromo-5,7-dimethoxy-1,2,4-triazolo[1,5-c]pyrimidine-2-sulfonamide: m.p., 212°-213° C. (dec.); and
N-(2,6-dichloro-3-methylphenyl)-8-bromo-5,7-dimethoxy-1,2,4-triazolo[1,5-c]pyrimidine-2-sulfonamide; m.p., 228°-229° C. (dec.).

EXAMPLE 15

Preparation of
N-(2,b-Dichlorophenyl-8-bromo-5-methoxy-1,2,4-triazolo[1,5-c-]pyrimidine-2-sulfonamide 2,6-Dichloroaniline (1.76 g, 10.9 mmol), 2-chlorosulfonyl-8-bromo-5-methoxy-1,2,4-triazolo[1,5-c]pyrimidine (1.5 g, 4.6 mmol), and 30 mL of dry acetonitrile were placed in a 100 mL flask equipped with a gas inlet adapter and a magnetic stir bar. Pyridine (0.74 mL, 9.2 mmol) and dimethyl sulfoxide (0.08 mL, 1.2 mmol) were added with stirring under nitrogen and the mixture was allowed to react for 1.25 hr. The volatiles were then removed by evaporation under reduced pressure and the residue was dissolved in 100 mL of methylene chloride. The solution obtained was extracted 3 times with 75 mL of 1N hydrochloric acid and once with 100 mL of water, dried over magnesium sulfate, filtered, and concentrated by evaporation under reduced pressure to obtain a yellow solid. This solid was diluted with 100 mL of hexane and, after standing 1 hr, the hexane was removed by filtration and the solids washed with more hexane and dried to obtain 1.1 g (52 percent of theory) of the title compound as a yellow solid melting at 192°-196° C.

Elemental Analysis for $C_{12}H_8BrCl_2N_5O_3S$:
Calculated: %C, 31.8: %H, 1.78; %N, 15.5.
Found: %C, 31.7: %H, 1.74; %N, 15.4.

EXAMPLE 16

Evaluation of Postemergence Herbicidal Activity

Representative compounds of Formula I were evaluated for the postemergence control of a variety of species of plants. In these evaluations the test plants were grown to a height of about 4 inches and were then sprayed to run-off with aqueous compositions containing known concentrations of the compounds using conventional spray equipment. The spray compositions were prepared by mixing the required amount of active ingredient and an emulsifier or dispersant in an aqueous acetone carrier to form an emulsion or suspension. Control plants were sprayed in the same manner with like compositions omitting the active ingredient. Thereafter, the plants were maintained in a greenhouse under conditions conducive to plant growth. Two weeks after treatment the plants were examined for growth and evaluated on a scale of 0 to 100 where 0 represents no effect and 100 represents complete kill. In this test 100 ppm represents about 0.25 Kg/Ha. The compounds and plant species tested, the application rates employed, and the results obtained in this test are given in Table 2.

TABLE 2

POSTEMERGENCE ACTIVITY, PERCENT CONTROL

| Cpd. No. | Rate, ppm | Coffee-weed | Cockle-bur | Jimson-weed | Morning Glory | Pigweed | Velvet Leaf | Corn | Rice | Wheat | Soy-beans | Yellow Nut-sedge |
|---|---|---|---|---|---|---|---|---|---|---|---|---|
| 1 | 7.8 | 95 | 100 | 100 | 10 | 90 | 70 | 60 | 90 | 70 | 100 | 90 |
| 2 | 31 | 100 | 100 | 60 | 75 | 90 | 80 | 0 | 0 | 0 | 90 | 0 |
| 3 | 250 | 100 | 85 | 80 | 80 | 100 | 80 | 70 | 50 | 20 | 60 | 80 |
| 4 | 250 | 100 | 80 | 80 | 75 | 100 | 70 | 0 | 0 | 0 | 50 | 0 |
| 7 | 3.9 | 100 | 80 | 88 | 90 | 70 | 87 | 83 | 80 | 40 | 90 | 100 |
| 9 | 7.8 | — | 100 | 90 | 100 | 80 | 95 | 0 | 50 | 0 | 90 | 85 |
| 12 | 63 | 80 | 100 | 90 | 80 | 75 | 93 | 0 | 0 | 0 | 75 | 50 |
| 13 | 15.6 | 100 | 100 | 100 | 100 | 90 | 85 | 70 | 10 | 80 | 90 | 90 |
| 19 | 63 | 100 | 100 | 90 | 90 | 85 | 100 | 85 | 85 | 70 | 88 | 88 |
| 20 | 15.6 | 50 | 90 | 95 | 90 | 40 | 90 | 80 | 20 | 20 | 40 | 50 |
| 21 | 15.6 | 85 | 97 | 85 | 99 | 45 | 99 | 83 | 30 | 0 | 83 | 99 |
| 23 | 2.0 | 75 | 100 | 93 | 99 | 80 | 80 | 0 | 93 | — | 85 | 90 |
| 25 | 3.9 | 83 | 100 | 97 | 100 | 50 | 97 | 0 | 0 | — | 10 | 90 |
| 26 | 7.8 | 85 | 88 | 88 | 85 | 100 | 90 | 85 | 15 | 40 | 90 | 50 |
| 28 | 15.6 | 100 | 100 | 95 | 100 | 80 | 90 | 90 | 90 | 65 | 90 | 100 |
| 30 | 500 | 100 | 100 | 70 | 90 | 85 | 95 | 0 | 0 | 0 | 85 | 85 |
| 31 | 1000 | 85 | 80 | 60 | 70 | 75 | 75 | 0 | — | 0 | 10 | 30 |
| 32 | 500 | 100 | 80 | 90 | 75 | 0 | 50 | 50 | — | — | — | — |
| 37 | 15.6 | 90 | 83 | 50 | 88 | 50 | 90 | 30 | 15 | 0 | 65 | 75 |
| 38 | 15.6 | 40 | 100 | 90 | 88 | 100 | 100 | 90 | 70 | 10 | 0 | 100 |
| 39 | 15.6 | 90 | 70 | 90 | 97 | 97 | 99 | 40 | 35 | 10 | 25 | 93 |
| 40 | 3.9 | 100 | 100 | 90 | 100 | 85 | 100 | 90 | 70 | 60 | 85 | 80 |
| 41 | 7.8 | 95 | 90 | 90 | 100 | 89 | 90 | 20 | 75 | 0 | 90 | 100 |
| 42 | 31 | 95 | 90 | 90 | 90 | 90 | 98 | 80 | 85 | 50 | 90 | 95 |

TABLE 2-continued
POSTEMERGENCE ACTIVITY, PERCENT CONTROL

| Cpd. No. | Rate. ppm | Coffee-weed | Cockle-bur | Jimson-weed | Morning Glory | Pigweed | Velvet Leaf | Corn | Rice | Wheat | Soy-beans | Yellow Nut-sedge |
|---|---|---|---|---|---|---|---|---|---|---|---|---|
| 43 | 16 | 95 | 95 | 75 | 90 | 50 | 85 | 0 | 0 | 0 | 90 | 78 |
| 44 | 1.9 | 100 | 90 | 88 | 89 | 25 | 85 | 20 | 45 | 70 | 90 | — |
| 45 | 125 | 70 | 100 | 90 | 90 | 100 | 90 | 90 | 85 | 100 | 90 | 95 |
| 46 | 7.8 | 95 | 100 | 100 | 75 | 30 | 75 | 100 | 50 | 75 | 75 | 85 |
| 47 | 3.9 | 90 | 100 | 100 | 90 | 85 | 70 | 70 | 100 | 75 | 93 | — |
| 48 | 63 | 90 | 100 | 100 | 100 | 100 | 95 | 90 | 100 | 95 | 90 | — |
| 49 | 16 | 100 | 100 | 60 | 80 | 90 | 70 | 0 | 40 | 0 | 80 | 0 |
| 50 | 250 | 100 | 100 | 90 | 85 | 100 | 85 | 80 | 40 | 40 | 70 | 85 |
| 51 | 125 | 95 | 100 | 85 | 80 | 100 | 85 | 90 | 60 | 20 | 80 | 80 |
| 52 | 250 | 100 | 100 | 100 | 90 | 100 | 100 | 90 | 40 | 70 | 70 | 70 |
| 53 | 125 | 100 | 90 | 100 | 90 | 100 | 80 | 60 | 20 | 50 | 70 | 50 |
| 54 | 125 | 95 | 100 | 90 | 80 | 90 | 80 | 50 | 30 | 50 | 80 | 0 |
| 55 | 31 | 90 | 90 | 85 | 85 | 75 | 80 | 20 | 70 | 40 | 90 | — |
| 56 | 16 | 88 | 90 | 88 | 100 | 75 | 65 | 35 | 80 | 50 | 90 | — |
| 57 | 500 | 70 | 40 | 70 | 30 | 30 | 70 | 0 | 0 | 0 | 35 | 0 |
| 58 | 250 | 98 | 100 | 30 | 70 | 0 | 70 | 0 | 0 | 0 | 80 | 0 |
| 59 | 500 | 95 | 100 | 80 | 70 | 0 | 75 | 0 | 0 | 0 | 25 | 70 |
| 62 | 16 | 95 | 95 | 95 | 90 | 20 | 80 | 25 | 0 | 0 | 0 | 0 |
| 63 | 500 | 95 | 100 | 95 | 90 | 95 | 90 | 0 | 0 | 15 | 80 | 20 |
| 64 | 125 | 90 | 85 | 95 | 80 | 80 | 85 | 0 | 50 | 0 | 70 | 20 |
| 65 | 7.8 | 88 | 88 | 95 | 100 | 85 | 90 | 55 | 50 | 75 | 88 | 70 |
| 66 | 16 | 85 | 88 | 75 | 100 | 75 | 90 | 10 | 0 | 20 | 86 | 0 |
| 67 | 31 | 90 | 100 | 88 | 100 | 90 | 95 | 65 | 35 | 20 | 88 | 70 |
| 68 | 7.8 | 85 | 100 | 98 | 100 | 85 | 90 | 0 | 50 | 20 | 88 | 60 |
| 69 | 3.9 | 88 | 90 | 45 | 90 | 45 | 85 | 0 | 0 | 0 | 70 | 0 |
| 70 | 16 | 88 | 88 | 85 | 90 | 55 | 88 | 0 | 0 | 0 | 85 | 40 |
| 71 | 7.8 | 88 | 100 | 60 | 90 | 85 | 85 | 0 | 10 | 0 | 88 | 0 |
| 72 | 1.0 | 75 | 100 | 100 | 100 | 0 | 90 | 75 | 35 | 0 | 10 | 65 |
| 73 | 15.6 | 93 | 90 | 99 | 80 | 95 | 99 | 55 | 80 | 40 | 15 | 100 |
| 74 | 1.0 | 88 | 90 | 75 | 85 | 30 | 70 | 30 | 0 | 40 | 40 | 40 |
| 75 | 7.8 | 90 | 95 | 80 | 100 | 75 | 70 | 0 | 0 | 0 | 65 | 0 |
| 76 | 16 | 100 | 90 | 85 | 100 | 90 | 80 | 65 | 75 | 45 | 90 | 88 |
| 77 | 7.8 | 85 | 100 | 90 | 100 | 90 | 90 | 5 | 70 | 35 | 75 | — |
| 78 | 63 | 70 | 100 | 80 | 80 | 85 | 80 | 0 | 40 | 10 | 70 | 85 |
| 79 | 16 | 80 | 80 | 80 | 0 | 80 | 80 | 0 | 20 | 50 | 50 | 75 |
| 80 | 63 | 90 | 90 | 80 | 90 | 80 | 80 | 0 | 0 | 0 | 75 | 70 |
| 81 | 7.8 | 90 | 85 | 90 | 80 | 95 | 80 | 0 | 80 | 90 | 60 | 60 |
| 82 | 16 | 100 | 100 | 100 | 80 | 100 | 90 | 70 | 40 | 60 | 70 | 80 |
| 83 | 3.9 | 100 | 90 | 65 | 75 | 65 | 70 | 0 | 0 | 0 | 60 | 65 |
| 84 | 500 | 50 | 70 | 60 | 50 | 70 | 30 | 40 | 25 | 40 | 80 | 20 |
| 85 | 7.8 | 75 | 100 | 80 | 85 | 75 | 80 | 30 | 0 | 30 | 50 | 70 |
| 86 | 31 | 90 | 100 | 85 | 85 | 15 | 45 | 25 | 20 | 0 | 75 | 80 |
| 87 | 16 | 80 | 90 | 80 | 80 | 75 | 80 | 0 | 20 | 0 | 35 | 75 |
| 88 | 125 | 100 | 90 | 90 | 80 | 100 | 100 | 50 | 85 | 60 | 80 | 85 |
| 89 | 250 | 100 | 100 | 80 | 80 | 95 | 100 | 75 | 45 | 70 | 70 | 85 |
| 90 | 31 | 90 | 90 | 80 | 90 | 85 | 85 | 60 | 40 | 40 | 75 | 85 |
| 91 | 3.9 | 88 | 90 | 70 | 90 | 80 | 90 | 70 | 75 | 85 | 85 | 90 |
| 92 | 16 | 88 | 95 | 70 | 100 | 70 | 90 | 0 | 15 | 30 | 88 | 70 |
| 93 | 63 | 88 | 85 | 98 | 100 | 80 | 98 | 0 | 90 | 85 | 88 | 100 |
| 94 | 16 | 80 | 100 | 80 | 50 | 85 | 88 | 75 | 20 | 40 | 88 | 50 |
| 95 | 31 | 90 | 95 | 88 | 100 | 0 | 70 | 28 | 40 | 0 | 88 | 90 |
| 96 | 3.9 | 80 | 100 | 85 | 85 | 70 | 80 | 40 | 40 | 15 | 20 | 85 |
| 97 | 2.0 | 80 | 90 | 70 | 85 | 70 | 80 | 20 | 60 | 10 | 35 | 70 |
| 98 | 7.8 | 75 | 85 | 90 | 90 | 80 | 88 | 40 | 70 | 40 | 0 | 95 |
| 99 | 31 | 75 | 90 | 95 | 100 | 99 | 100 | 75 | 95 | 60 | 90 | — |
| 100 | 16 | 95 | 100 | 70 | 90 | 50 | 85 | 0 | 0 | 0 | 90 | 70 |
| 101 | 3.9 | 100 | 90 | 100 | 85 | 65 | 90 | 0 | 60 | 0 | 90 | 100 |
| 102 | 125 | 90 | 95 | 90 | 100 | 100 | 95 | 100 | 90 | 98 | 90 | 100 |
| 103 | 63 | 90 | 95 | 75 | 90 | 85 | 90 | 45 | 95 | 100 | 90 | 95 |
| 105 | 15.6 | 100 | 90 | 70 | 95 | 70 | 95 | 0 | 0 | 0 | 90 | 75 |
| 106 | 7.8 | 100 | 80 | 95 | 100 | 99 | 97 | 99 | 60 | 50 | 70 | 99 |
| 107 | 15.6 | 100 | 100 | 95 | 100 | 90 | 98 | 20 | 75 | 0 | 90 | 90 |

EXAMPLE 17

Evaluation of Preemergence Herbicidal Activity

Representative compounds of Formula I were evaluated for the preemergence control of a variety of species of plants. In these evaluations, seeds were planted in pots in an agricultural soil and immediately thereafter measured quantities of the test chemical were drenched onto the soil surface as an aqueous emulsion or suspension and allowed to leach into the soil. The aqueous emulsions or suspensions were prepared by mixing the required amount of active ingredient in an aqueous acetone carrier containing 0.1 percent by weight surface-active agent. Control pots were drenched with a like mixture omitting the active ingredient. The pots were maintained in a greenhouse under conditions conducive to germination and growth. About 2 weeks after treatment the test was graded on a scale of 0–100 where 0 represents no effect and 100 represents complete kill. The plant species and compounds tested, the application rates employed, and the results obtained in this test are given in Table 3.

TABLE 3

PREMERGENCE ACTIVITY, PERCENT CONTROL

| Cpd. No. | Rate, Kg/Ha | Black Night-shade | Morning Glory | Pigweed | Velvet Leaf |
|---|---|---|---|---|---|
| 1 | 11 | 100 | 90 | 95 | 100 |
| 2 | 11 | 100 | 100 | 0 | 0 |
| 29 | 11 | 65 | 90 | 100 | 0 |
| 30 | 11 | 90 | 90 | 100 | 100 |
| 31 | 11 | 90 | 80 | 90 | 80 |
| 32 | 11 | 60 | 80 | 100 | 100 |
| 41 | 11 | 100 | 100 | 100 | 100 |
| 42 | 11 | 100 | 100 | 100 | 100 |
| 44 | 0.14 | 80 | 85 | 95 | 85 |
| 46 | 0.28 | — | 90 | 97 | 65 |
| 48 | 0.14 | 85 | 80 | 95 | 85 |
| 49 | 0.56 | — | 90 | 99 | 80 |
| 51 | 0.28 | — | 95 | 100 | 90 |
| 53 | 0.07 | — | 10 | 100 | 90 |
| 56 | 0.14 | 100 | 80 | 80 | 70 |
| 59 | 11 | 70 | 90 | 20 | 80 |
| 62 | 0.14 | — | 80 | 99 | 80 |
| 64 | 11 | 100 | 98 | 100 | 100 |
| 66 | 0.14 | 65 | 80 | 75 | 90 |
| 67 | 0.14 | 85 | 80 | 95 | 85 |
| 68 | 0.14 | 85 | 80 | 85 | 80 |
| 70 | 0.28 | 50 | 90 | 75 | 50 |
| 74 | 0.07 | — | 100 | 95 | 100 |
| 75 | 0.14 | — | 85 | 90 | 85 |
| 76 | 0.14 | — | 90 | 99 | 95 |
| 77 | 0.14 | 85 | 80 | 95 | 85 |
| 78 | 0.07 | — | 95 | 99 | 95 |
| 80 | 0.56 | — | 80 | 70 | 90 |
| 81 | 0.14 | — | 100 | 100 | 80 |
| 82 | 0.07 | — | 97 | 90 | 99 |
| 84 | 11 | 90 | 90 | 95 | 75 |
| 88 | 11 | 90 | 100 | 100 | 98 |
| 89 | 0.28 | — | 90 | 99 | 85 |
| 90 | 11 | 98 | 100 | 100 | 100 |
| 91 | 0.02 | 85 | 70 | 85 | 95 |
| 93 | 0.28 | 90 | 75 | 90 | 70 |
| 94 | 0.14 | 90 | 75 | 75 | 85 |
| 96 | 0.14 | 85 | 80 | 95 | 85 |
| 97 | 0.14 | 100 | 75 | 100 | 85 |
| 98 | 0.07 | 80 | 80 | 80 | 85 |
| 99 | 0.14 | 95 | 85 | 100 | 85 |
| 101 | 0.14 | 80 | 80 | 100 | 95 |
| 102 | 11 | 100 | 95 | 100 | 95 |

What is claimed is:

1. A 1,2,4-triazolo[1,5-c]pyrimidine-2-sulfonamide compound of the formula

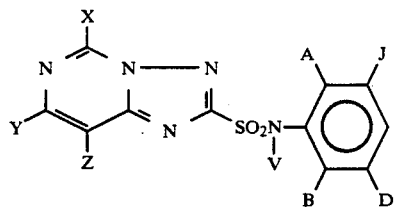

wherein

X represents $OCH_3$ or $OC_2H_5$;

Y and Z each, independently represent $OCH_3$, $OC_2H_5$, H, $CH_3$, Cl, Br, or F;

A represents F, Cl, Br, C(O)E, $C_1$–$C_4$ haloalkyl, $NO_2$, CN, $SOR^3$, or $SO_2R^3$;

B represents H, R, F, Cl, Br, CN, $OR^3$, $SR^3$, $NR^1R^2$, phenyl, phenoxy, or phenylthio, each phenyl, phenoxy, and phenylthio optionally possessing 1 to 3 substituents selected from the group consisting of F, Cl, Br, CN, $CF_3$, $NO_2$, and $CH_3$;

D and J each represent H or $CH_3$, with the proviso that at least one of D and J represents H;

V represents H or $C(O)R^3$;

R represents $C_1$–$C_3$ alkyl;

$R^1$ and $R^2$ each, independently represent H or $C_1$–$C_4$ alkyl;

$R^3$ represents $C_1$–$C_4$ alkyl or $C_1$–$C_4$ haloalkyl;

E represents $OR^1$ or $NR^1R^2$; and, when V represents H, an agriculturally acceptable salt thereof.

2. A compound according to claim 1 wherein V represents H or an agriculturally acceptable salt thereof.

3. A compound according to claim 2 wherein Y and Z each, independently represent H, $OCH_3$, Cl, Br, or F.

4. A compound according to claim 2 wherein one of Y and Z represents $CH_3$, $OCH_3$, Cl, F, or Br and the other represents H.

5. A compound according to claim 2 wherein A represents F, Cl, Br, C(O)E, $CF_3$, or $NO_2$.

6. A compound according to claim 2 wherein B represents H, $CH_3$, F, Cl, Br, $OCH_3$, or $SCH_3$.

7. A compound according to claim 2 wherein J represents H and D represents H or $CH_3$.

8. A compound according to claim 2 wherein one of Y and Z represents $CH_3$, $OCH_3$, Cl, Br, or F and the other represents H; A represents F, Cl, Br, C(O)E, $CF_3$, or $NO_2$; B represents H, $CH_3$, F, Cl, Br, $OCH_3$, or $SCH_3$; J represents H; and D represents H or $CH_3$.

9. A compound according to claim 8, N-(2,6-dichloro-3-methylphenyl)-5,7-dimethoxy-1,2,4-triazolo[1,5-c]pyrimidine-2-sulfonamide.

10. A compound according to claim 8, N-(2-methoxycarbonyl-6-fluorophenyl)-7-chloro-5-methoxy-1,2,4-triazolo[1,5-c]pyrimidine-2-sulfonamide.

11. A compound according to claim 8, N-(2-methoxycarbonyl-6-chlorophenyl)-7-fluoro-5-ethoxy-1,2,4-triazolo[1,5-c]pyrimidine-2-sulfonamide.

12. A compound according to claim 8, N-(2-chloro-6-fluorophenyl)-5-ethoxy-7-fluoro-1,2,4-triazolo[1,5-c]pyrimidine-2-sulfonamide.

13. A compound according to claim 8, N-(2,6-dichlorophenyl)-7-fluoro-5-ethoxy-1,2,4-triazolo[1,5-c]pyrimidine-2-sulfonamide.

14. A compound according to claim 8, N-(2,6-difluorophenyl)-8-fluoro-5-methoxy-1,2,4-triazolo[1,5-c]pyrimidine-2-sulfonamide.

15. A compound according to claim 8, N-(2,6-difluorophenyl)-8-chloro-5-methoxy-1,2,4-triazolo[1,5-c]pyrimidine-2-sulfonamide.

16. A compound according to claim 8, N-(2-methoxycarbonyl-6-fluorophenyl)-8-fluoro-5-methoxy-1,2,4-triazolo[1,5-c]pyrimidine-2-sulfonamide.

17. An herbicidal composition comprising an agriculturally acceptable adjuvant or carrier and an herbicidally effective amount of a 1,2,4-triazolo[1,5-c]pyrimidine-2-sulfonamide compound of the formula

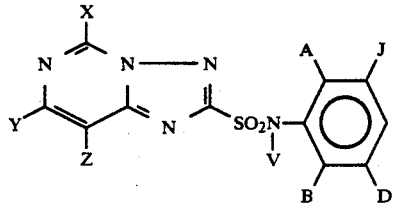

wherein

X represents $OCH_3$ or $OC_2H_5$;

Y and Z each, independently represent OCH$_3$, OC$_2$H$_5$, H, CH$_3$, Cl, Br, or F;

A represents F, Cl, Br, C(O)E, C$_1$–C$_4$ haloalkyl, NO$_2$, CN, SOR$^3$, or SO$_2$R$^3$;

B represents H, R, F, Cl, Br, CN, OR$^3$, SR$^3$, NR$^1$R$^2$, phenyl, phenoxy, or phenylthio, each phenyl, phenoxy, and phenylthio optionally containing 1 to 3 substituents selected from the group consisting of F, Cl, Br, CN, CF$_3$, NO$_2$, and CH$_3$;

D and J each represent H or CH$_3$, with the proviso that at least one of D and J represents H;

V represents H or C(O)R$^3$;

R represents C$_1$–C$_3$ alkyl;

R$^1$ and R$^2$ each, independently represent H or C$_1$–C$_4$ alkyl;

R$^3$ represents C$_1$–C$_4$ alkyl or C$_1$–C$_4$ haloalkyl;

E represents OR$^1$ or NR$^1$R$^2$; and, when V represents H, an agriculturally acceptable salt thereof.

18. A composition according to claim 17 wherein V represents H and an agriculturally acceptable salt thereof.

19. A composition according to claim 18 wherein Y and Z each, independently represent H, OCH$_3$, Cl, Br, or F.

20. A composition according to claim 18 wherein one of Y and Z represents CH$_3$, OCH$_3$, Cl, F, or Br and the other represents H.

21. A composition according to claim 18 wherein A represents F, Cl, Br, C(O)E, CF$_3$, or NO$_2$.

22. A composition according to claim 18 wherein B represents H, CH$_3$, F, Cl, Br, OCH$_3$, or SCH$_3$.

23. A composition according to claim 18 wherein J represents H and D represents H or CH$_3$.

24. A composition according to claim 18 wherein one of Y and Z represents CH$_3$, OCH$_3$, Cl, Br, or F and the other represents H; A represents F, Cl, Br, C(O)E, CF$_3$, or NO$_2$; B represents H, CH$_3$, F, Cl, Br, OCH$_3$, or SCH$_3$; J represents H; and D represents H or CH$_3$.

25. A composition according to claim 24 wherein the compound is N-(2,6-dichloro-3-methylphenyl)-5,7-dimethoxy-1,2,4-triazolo[1,5-c]pyrimidine-2-sulfonamide or an agriculturally acceptable salt thereof.

26. A composition according to claim 24 wherein the compound is N-(2-methoxycarbonyl-6-fluorophenyl)-7-chloro-5-methoxy-1,2,4-triazolo[1,5-c]pyrimidine-2-sulfonamide or an agriculturally acceptable salt thereof.

27. A composition according to claim 24 wherein the compound is N-(2-methoxycarbonyl-6-chlorophenyl)-7-fluoro-5-ethoxy-1,2,4-triazolo[1,5-c]pyrimidine-2-sulfonamide or an agriculturally acceptable salt thereof.

28. A composition according to claim 24 wherein the compound is N-(2-chloro-6-fluorophenyl)-5-ethoxy-7-fluoro-1,2,4-triazolo[1,5-c]pyrimidine-2-sulfonamide or an agriculturally acceptable salt thereof.

29. A composition according to claim 24 wherein the compound is N-(2,6-dichlorophenyl)-7-fluoro-5-ethoxy-1,2,4-triazolo[1,5-c]pyrimidine-2-sulfonamide or an agriculturally acceptable salt thereof.

30. A composition according to claim 24 wherein the compound is N-(2,6-difluorophenyl)-8-fluoro-5-methoxy-1,2,4-triazolo[1,5-c]pyrimidine-2-sulfonamide or an agriculturally acceptable salt thereof 31. A composition according to claim 24 wherein the compound is N-(2,6-difluorophenyl)-8-chloro-5-methoxy-1,2,4-triazolo[1,5-c]pyrimidine-2-sulfonamide or an agriculturally acceptable salt thereof.

32. A composition according to claim 24 wherein the compound is N-(2-methoxycarbonyl-6-fluorophenyl)-8-fluoro-5-methoxy-1,2,4-triazolo[1,5-c]pyrimidine-2-sulfonamide or an agriculturally acceptable salt thereof.

33. A method of controlling unwanted vegetation which comprises applying to the vegetation or to the locus of the vegetation an herbicidally effective amount a 1,2,4-triazolo[1,5-c]pyrimidine-2-sulfonamide compound of the formula

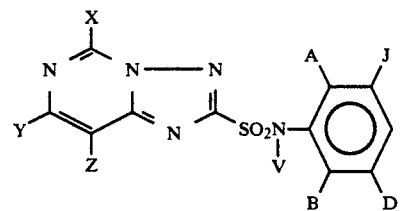

wherein

X represents OCH$_3$ or OC$_2$H$_5$;

Y and Z each, independently represent OCH$_3$, OC$_2$H$_5$, H, CH$_3$, Cl, Br, or F;

A represents F, Cl, Br, C(O)E, C$_1$–C$_4$ haloalkyl, NO$_2$, CN, SOR$^3$, or SO$_2$R$^3$;

B represents H, R, F, Cl, Br, CN, OR$^3$, SR$^3$, NR$^1$R$^2$, phenyl, phenoxy, or phenylthio, each phenyl, phenoxy, and phenylthio optionally containing 1 to 3 substituents selected from the group consisting of F, Cl, Br, CN, CF$_3$, NO$_2$, and CH$_3$;

D and J each represent H or CH$_3$, with the proviso that at least one of D and J represents H;

V represents H or C(O)R$^3$;

R represents C$_1$–C$_3$ alkyl;

R$^1$ and R$^2$ each, independently represent H or C$_1$–C$_4$ alkyl;

R$^3$ represents C$_1$–C$_4$ alkyl or C$_1$–C$_4$ haloalkyl;

E represents OR$^1$ or NR$^1$R$^2$; and, when V represents H, an agriculturally acceptable salt thereof.

34. A method according to claim 33 wherein V represents H and an agriculturally acceptable salt thereof.

35. A method according to claim 34 wherein Y and Z each, independently represent H, OCH$_3$, Cl, Br, or F.

36. A method according to claim 34 wherein one of Y and Z represents CH$_3$, OCH$_3$, Cl, F, or Br and the other represents H.

37. A method according to claim 34 wherein A represents F, Cl, Br, C(O)E, CF$_3$, or NO$_2$.

38. A method according to claim 34 wherein B represents H, CH$_3$, F, Cl, Br, OCH$_3$, or SCH$_3$.

39. A method according to claim 34 wherein J represents H and D represents H or CH$_3$.

40. A method according to claim 34 wherein one of Y and Z represents CH$_3$, OCH$_3$, Cl, Br, or F and the other represents H; A represents F, Cl, Br, C(O)E, CF$_3$, or NO$_2$; B represents H, CH$_3$, F, Cl, Br, OCH$_3$, or SCH$_3$; J represents H; and D represents H or CH$_3$.

41. A method according to claim 40 wherein the compound is N-(2,6-dichloro-3-methylphenyl)-5,7-dimethoxy-1,2,4-triazolo[1,5-c]pyrimidine-2-sulfonamide or an agriculturally acceptable salt thereof.

42. A method according to claim 40 wherein the compound is N-(2-methoxycarbonyl-6-fluorophenyl)-7-chloro-5-methoxy-1,2,4-triazolo[1,5-c]pyrimidine-2-sulfonamide or an agriculturally acceptable salt thereof.

43. A method according to claim 40 wherein the compound is N-(2-methoxycarbonyl-6-chlorophenyl)-7-fluoro-5-ethoxy-1,2,4-triazolo[1,5-c]pyrimidine-2-sulfonamide or an agriculturally acceptable salt thereof.

44. A method according to claim 40 wherein the compound is N-(2-chloro-6-fluorophenyl)-5-ethoxy-7-fluoro-1,2,4-triazolo[1,5-c]pyrimidine-2-sulfonamide or an agriculturally acceptable salt thereof.

45. A method according to claim 40 wherein the compound is N-(2,6-dichlorophenyl)-7-fluoro-5-ethoxy-1,2,4-triazolo[1,5-c]pyrimidine-2-sulfonamide or an agriculturally acceptable salt thereof.

46. A method according to claim 40 wherein the compound is N-(2,6-difluorophenyl)-8-fluoro-5-methoxy-1,2,4-triazolo[1,5-c]pyrimidine-2-sulfonamide or an agriculturally acceptable salt thereof.

47. A method according to claim 40 wherein the compound is N-(2,6-difluorophenyl)-8-chloro-5-methoxy-1,2,4-triazolo[1,5-c]pyrimidine-2-sulfonamide or an agriculturally acceptable salt thereof.

48. A composition according to claim 40 wherein the compound is N-(2-methoxycarbonyl-6-fluorophenyl)-8-fluoro-5-methoxy-1,2,4-triazolo[1,5-c]pyrimidine-2-sulfonamide or an agriculturally acceptable salt thereof.

49. A method according to claim 33 wherein the compound is applied preemergently.

50. A method according to claim 33 wherein the compound is applied postemergently.

51. A method of controlling unwanted vegetation in crops which comprises applying to the vegetation or to the locus of the vegetation a selective and herbicidally effective amount of a selectively effective 1,2,4-triazolo[1,5-c]pyrimidine-2-sulfonamide compound of the formula

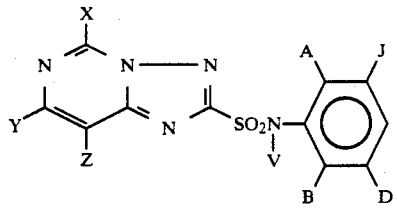

wherein

X represents $OCH_3$ or $OC_2H_5$;

Y and Z each, independently represent $OCH_3$, $OC_2H_5$, H, $CH_3$, Cl, Br, or F;

A represents F, Cl, Br, C(O)E, $C_1-C_4$ haloalkyl, $NO_2$, CN, $SOR^3$, or $SO_2R^3$;

B represents H, R, F, Cl, Br, CN, $OR^3$, $SR^3$, $NR^1R^2$, phenyl, phenoxy, or phenylthio, each phenyl, phenoxy, and phenylthio optionally containing 1 to 3 substituents selected from the group consisting of F, Cl, Br, CN, $CF_3$, $NO_2$, and $CH_3$;

D and J each represent H or $CH_3$, with the proviso that at least one of D and J represents H;

V represents H or $C(O)R^3$;

R represents $C_1-C_3$ alkyl;

$R^1$ and $R^2$ each, independently represent H or $C_1-C_4$ alkyl;

$R^3$ represents $C_1-C_4$ alkyl or $C_1-C_4$ haloalkyl;

E represents $OR^1$ or $NR^1R^2$; and, when V represents H, an agriculturally acceptable salt thereof.

52. A method according to claim 51 wherein V represents H and an agriculturally acceptable salt thereof.

53. A method according to claim 52 wherein one of Y and Z represents $CH_3$, $OCH_3$, Cl, Br, or F and the other represents H; A represents F, Cl, Br, C(O)E, $CF_3$, or $NO_2$; B represents H, $CH_3$, F, Cl, Br, $OCH_3$, or $SCH_3$; J represents H; and D represents H or $CH_3$.

54. A method according to claim 52 wherein the crop is wheat.

55. A method according to claim 52 wherein the crop is corn.

56. A method according to claim 52 wherein the crop is rice.

57. A method according to claim 52 wherein crop is soybeans.

58. A method according to claim 51 wherein the compound is applied postemergently.

59. A compound of the formula

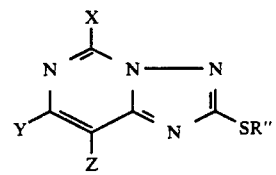

wherein

X represents $OCH_3$, $OC_2H_5$, or Cl;

Y and Z each, independently represent $OCH_3$, $OC_2H_5$, H, $CH_3$, Cl, Br, or F; and R" represents benzyl or $C_2-C_4$ alkyl.

60. A compound according to claim 59 wherein one of Y and Z each, independently represent H, $OCH_3$, Cl, Br, or F.

61. A compound according to claim 59 wherein one of Y and Z represents $CH_3$, $OCH_3$, Cl, F, or Br and the other represents H.

62. A compound according to claim 61, 2-benzylthio-7-chloro-5-methoxy-1,2,4-triazolo[1,5-c]pyrimidine.

63. A compound according to claim 61, 2-benzylthio-8-fluoro-5-methoxy-1,2,4-triazolo[1,5-c]pyrimidine.

64. A compound according to claim 61, 2-benzylthio-7-fluoro-5-ethoxy-1,2,4-triazolo[1,5-c]pyrimidine.

65. A compound according to claim 61, 2-benzylthio-8-chloro-5-methoxy-1,2,4-triazolo[1,5-c]pyrimidine.

66. A sulfonyl chloride compound of the formula

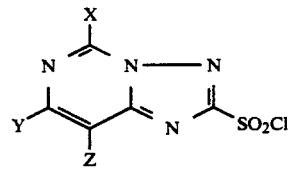

wherein

X represents $OCH_3$, $OC_2H_5$, or Cl; and

Y and Z each, independently represent $OCH_3$, $OC_2H_5$, H, $CH_3$, Cl, Br, or F.

67. A compound according to claim 66 wherein Y and Z each, independently represent H, $OCH_3$, Cl, Br, or F.

68. A compound according to claim 66 wherein one of Y and Z represents $CH_3$, $OCH_3$, Cl, F, or Br and the other represents H.

69. A compound according to claim 68, 5-chloro-2-chlorosulfonyl-7-methoxy-1,2,4-triazolo[1,5-c]pyrimidine.

70. A compound according to claim 68, 7-chloro-2-chlorosulfonyl-5-methoxy-1,2,4-triazolo[1,5-c]pyrimidine.

71. A compound according to claim 68, 2-chlorosulfonyl-8-fluoro-5-methoxy-1,2,4-triazolo[1,5-c]pyrimidine.

72. A compound according to claim 68, 2-chlorosulfonyl-5-ethoxy-7-fluoro-1,2,4-triazolo[1,5-c]pyrimidine.

73. A compound according to claim 68, 8-chloro-2-chlorosulfonyl-5-methoxy-1,2,4-triazolo[1,5-c]pyrimidine.

* * * * *